US007067552B2

(12) United States Patent
Holton et al.

(10) Patent No.: US 7,067,552 B2
(45) Date of Patent: Jun. 27, 2006

(54) RADIOSENSITIZING TAXANES AND THEIR PHARMACEUTICAL PREPARATIONS

(75) Inventors: Robert A. Holton, Tallahassee, FL (US); Hossain Nadizadeh, Fairfield, NJ (US); Li-Xi Yang, Tallahassee, FL (US)

(73) Assignee: Florida State University, Tallahassee, FL (US)

( * ) Notice: Subject to any disclaimer, the term of this patent is extended or adjusted under 35 U.S.C. 154(b) by 303 days.

(21) Appl. No.: 09/978,436

(22) Filed: Oct. 16, 2001

(65) Prior Publication Data

US 2002/0040155 A1 Apr. 4, 2002

Related U.S. Application Data

(63) Continuation of application No. 09/723,719, filed on Nov. 28, 2000, now abandoned, which is a continuation of application No. 09/129,647, filed on Aug. 5, 1998, now abandoned, which is a continuation of application No. 08/710,240, filed on Sep. 13, 1996, now abandoned.

(60) Provisional application No. 60/003,687, filed on Sep. 13, 1995.

(51) Int. Cl.
*A61K 31/337* (2006.01)
*C07D 305/14* (2006.01)

(52) U.S. Cl. ............. 514/449; 549/510; 549/511; 548/311.4; 514/397

(58) Field of Classification Search .............. 549/510, 549/511; 514/449, 397; 548/311.4
See application file for complete search history.

(56) References Cited

U.S. PATENT DOCUMENTS

| 5,250,683 A | 10/1993 | Holton et al. |
| 5,283,253 A | 2/1994 | Holton et al. |
| 5,648,506 A | 7/1997 | Desai et al. |

OTHER PUBLICATIONS

Tishler, et al., "Taxol: A Novel Radiation Sensitizer," Int. J. Radiat. Oncol. Biol. Phys., 1992, vol. 22, pp. 613–617.
Tishler, "Taxol Sensitizes Human Astrocytoma Cells to Radiation," Cancer Res., 1992, vol. 52, pp. 3495–3497.
Steren, et al., "Taxol Sensitizes Human Ovarian Cancer Cells to Radiation," Gynecol. Oncol., 1993, vol. 48, pp 252–258.
Steren, et al., "Taxol as a Radiation Sensitizer: A Flow Cytometric Study," Gynecol. Oncol., 1993, vol. 50, pp. 89–93.
Hei, et al., "Taxol, Radiation, and Oncogenic Transformation," Gynecol. Oncol., 1993, vol. 53, pp. 1368–1372.
Liebmann, et al., "Changes in Radiation Survival Curve Parameters in Human Tumor and Rodent Cells Exposed to Paclitaxel (Taxol®)," Int. J. Radiat. Oncol. Boil. Phys., 1994, vol. 29, No. 3, pp. 559–564.
Liebmann, et al., "In Vitro Studies of Taxol as a Radiation Sensitizer in Human Tumor Cells," I. Natl. Cancer, 1994, vol. 86, No. 6, pp. 441–446.
Milas, et al., "Enhancement of Tumor Radioresponse of a Murine Mammaray Carcinoma by Paclitaxel," Cancer Research, 1994, vol. 54, pp. 3506–3510.
Bocian, et al., "Sister chromatid exchanges induced by two radiosensitizing platinum compounds (cis–dichloro–bis isopropylamine transdihydroxy platinum IV (CHIP) and cis platinum metronoidaxole$_2$ Cl$_2$ (FLAP)) in CHO cells in vitro," Br. J. Cancer, 1983, vol. 48, pp. 803–807.
Teicher, et al., "Radiosensitization of EMT6 Cells by Four Platinum Complexes," Int. J. Radiat. Oncol. Biol. Phys., 1985, vol. 11, pp. 937–941.
Skov, et al., "Platinum Complexes with One Radiosensitizing Ligand [PtCl$_2$NH$_3$) (Sensitizer)]: Radiosensitization and Toxicity Studies in Vitro," Radiat. Res., 1987, vol. 112, pp. 273–282.
Skov, et al., "Toxicity of [PtCl$_2$(NH$_3$)L] in hypoxia; L=misonidazole or metronidazole," Anticancer Drug Dis., 1990, vol. 5, pp. 121–128.
Skov, et al., "Radiosensitization by metal complexes of 4(5)–nitroimidazole," Int. J. Radiat. Biol., 1990, vol. 57, pp. 947–958.
Herman, et al., "Effect of Hypoxia and Acidosis on the Cytotoxicity of Four Platinum Complexes at Normal and Hyperthermic Temperatures," Cancer Res., 1988, vol. 48, pp. 2342–2347.
Carboni, et al., "Synthesis of a Photoaffinity Analog of Taxol as an Approach to Identify the Taxol Binding Site on Microtubules," J. Med. Chem., 1993, vol. 36, pp. 513–515.
Chen, et al., "Structure–Activity Relationships of Taxol® Synthesis and Biological Evaluation of C2 Taxol Analogs," Bioorg. & Med. Chem. Lett., 1994, vol. 4, No. 3, pp. 479–482.
Rimoldi, et al., "Modified Taxols, 9. Synthesis and Biological Evaluation of 7–Substituted Photoaffinity Analogues of Taxol," J. Nat. Prod., 1993, vol. 56, pp. 1313–1330.
Kingston, D. G. I., "The Chemistry of Taxol," Pharmacol. Ther., 1991, vol. 52, pp. 1–34.
Kingston, D. G. I., "Taxol: The Chemistry and Structure–Activity Relationships of a Novel Anticancer Agent," Trends Biotechnol., 1994, vol. 12, pp. 222–227.
Nicolaou, et al., "Chemistry and Biology of Taxol," Angew. Chem. Int. Ed. Engl., 1994, vol. 33, pp. 15–44.
Kingston, et al., "The Chemistry of Taxol, A Clinically Useful Anticancer Agent," J. Nat. Prod., 1990, vol. 53, No. 1, pp. 1–12.
Guenard, et al. "Taxol and Taxotere: Discovery, Chemistry, and Structure–Activity Relationships," Acc. Chem. Res., 1993, vol. 26, pp. 160–167.

(Continued)

*Primary Examiner*—Bernard Dentz
(74) *Attorney, Agent, or Firm*—Senniger Powers

(57) ABSTRACT

Taxanes containing electron-affinic radiosensitizing functional groups, their pharmaceutical preparations, and methods of making and using this new class of highly potent radiosensitizers of tumor cells.

17 Claims, 18 Drawing Sheets

OTHER PUBLICATIONS

Commercon, et al., "Partial Synthesis of Major Human Metabolites of Docetaxel," Tetrahedron, 1994, vol. 50, No. 34, pp. 10289–10298.

Stratford, I. J., "Mechanisms of Hypoxic Cell Radiosensitization and the Development of New Sensitizers," Int. J. Radiat. Oncol. Biol. Phys., 1982, vol. 8, pp. 391–398.

Biaglow, et al. "The Effects of Nitrobenzene Derivatives on Oxygen Utilization and Radiation Response of an in Vitro Tumor Model," Radiat. Res., 1976, vol. 65, pp. 529–539.

The Board of Education (for an on behalf of the Trustees of Florida State University), et al. v. American Bioscience, Inc. and Chunlin Tao, United States Court of Appeal for the Federal Circuit Court Decision, Case No. 02–1109, Decided Jun. 23, 2003, 22 pages.

RADIOSENSITIZING TAXANES AND THEIR PHARMACEUTICAL PREPARATIONS

This application is a continuation of Ser. No. 09/723,719 filed Nov. 28, 2000, now abandoned, which is a continuation of Ser. No. 09/129,647 filed Aug. 5, 1998, now abandoned which is a continuation of 08/710,240 filed Sep. 13, 1996, now abandoned, which claims benefit of provisional application No. 60/003,687, filed on Sep. 13, 1995.

BACKGROUND OF THE INVENTION

This invention relates to novel radiosensitizing compounds, and in particular, to substituted taxanes containing radiosensitizing moieties, their pharmaceutical preparations, and methods of using this new class of highly potent radiosensitizers of tumor cells.

In the United States alone, over a half million patients undergo radiation therapy each year as a part of their battle against cancer. To date, however, radiation therapy has produced only limited success as a cancer treatment. Understandably, therefore, a major effort has been underway for a number of years to develop means to improve the efficacy of such radiotherapy techniques.

It is widely believed that the presence of radioresistant, hypoxic (poorly oxygenated) cells in tumors constitutes a significant factor in causing local failure in conventional cancer radiotherapy. For example, it was reported by Gatenby et al., *Int. J. Radiat. Oncol. Biol. Phys.* 14: 831–833 (1988), that for head and neck tumors, the hypoxic cell volume is inversely correlated with tumor radiosensitivity. Other reports confirm this conclusion for a variety of types of tumors and suggest that the presence of a concentration of as little as 2–3% hypoxic cells in a tumor may double the radiation dose required for tumor control.

Various solutions have been proposed to overcome the problem of hypoxia, including carrying out radiation treatments in high pressure oxygen chambers and the substitution of "fast neutron" or π meson radiation in place of X-rays. However, these techniques are not wholly satisfactory for a number of reasons, including the great expense and difficulty frequently associated with such procedures.

One promising field of investigation for dealing with radioresistant hypoxic tumor cells has been the use of "radiosensitizing" compounds which selectively increase the sensitivity of hypoxic cells to radiation. This specificity to hypoxic cells is also valuable because a significant percentage of solid tumors are characterized by such cells while most normal tissue is not. Thus, treatment with such compounds serves to enhance the impact of radiation on tumor cells while having little effect on the impact of radiation on healthy cell tissue. A number of heterocyclic, electron-affinic compounds, and in particular, those with oxidized nitrogen moieties, have been successfully used for the purpose of radiosensitizing hypoxic tumor cells. Specifically, the discovery that the nitroimidazoles, metronidazole (metro) and misonidazole (miso), sensitize hypoxic cells to radiation provided initial optimism for a breakthrough solution to the problem of tumor hypoxia. Unfortunately, however, both agents have proven to be highly toxic at therapeutic levels.

The possibility of using chemotherapeutic agents to selectively enhance radiation response in tumors has also been proposed. In addition to its use a chemotherapeutic agent, taxol, for example, has been investigated in vitro and in vivo as a potential radiosensitizing drug. See, Tishler et al., *Radiation Oncology Biol. Phys.*, 22:613–617 (1992); Tishler et al., *Cancer Research,* 52:3495–3497 (1992); Steren, et al., *Gynecologic Oncology,* 48:252–258 (1993); Steren, et al., *Gynecologic Oncology,* 50:89–93 (1993); Choy et al., *Cancer,* 71:3774–3778 (1993); Milas et al., *Cancer Research,* 54:3506–3510 (1994); and Joschko et al., *Proceedings of the American Association for Cancer Research,* 35:647 (1994). Although the reported data suggests that taxol is an effective radiosensitizer, recent data from our laboratory leads us to question whether the reported data has been misinterpreted. In any event, a need continues to exist for compounds which possess antitumor activity and which are more potent radiosensitizers and thus, can be administered at lower doses to reduce toxic side effects.

SUMMARY OF THE INVENTION

Among the several objects of the invention, therefore, may be noted the provision of a novel class of compounds and pharmaceutical preparations containing them which possess antitumor activity and which are potent radiosensitizing agents for cancer radiation therapy. Also among the objects of the invention are methods for the use of such compounds and pharmaceutical preparations in warm-blooded animals in radiation therapy.

Briefly, therefore, the present invention is directed to taxanes comprising one or more electron-affinic moieties. Such compounds provide greatly enhanced radiosensitization of tumors and reduced toxic side effects to normal body tissues at a given dosage as compared to conventional radiosensitization agents. The electron-affinic moiety may be attached directly, or indirectly through a linker to one of the ring atoms of the taxane or to one of the C13 side chain atoms. For example, the electron-affinic moiety may be attached to the C2, C4, C7, C9, C10, C14, C3' or C5' carbon of a taxane corresponding to the structure:

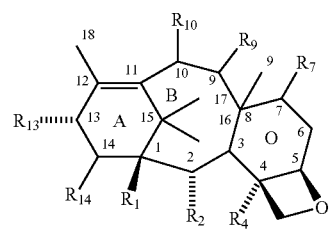

wherein

M comprises ammonium or is a metal;

$R_1$ is hydrogen or hydroxy;

$R_2$ is —$OT_2$, —$OCOZ_2$, —$OCOOZ_2$, $RSG_1$ or $RSG_2$;

$R_4$ is —$OT_4$, —$OCOZ_4$, —$OCOOZ_4$, $RSG_1$ or $RSG_2$;

$R_7$ is hydrogen, halogen, —$OT_7$, —$OCOZ_7$, —$OCOOZ_7$, $RSG_1$ or $RSG_2$;

$R_9$ is hydrogen, keto, —$OT_9$, —$OCOZ_9$, —$OCOOZ_9$, $RSG_1$ or $RSG_2$;

$R_{10}$ is hydrogen, keto, —$OT_{10}$, —$OCOZ_{10}$, —$OCOOZ_{10}$, $RSG_1$ or $RSG_2$;

$R_7$, $R_9$, and $R_{10}$, independently have the alpha or beta stereochemical configuration;

$R_{13}$ is hydroxy, protected hydroxy, keto, MO— or

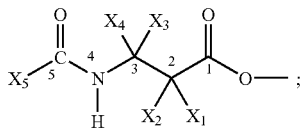

$R_{14}$ is hydrogen, hydroxy, protected hydroxy, $RSG_1$ or $RSG_2$;

$T_2$, $T_4$, $T_7$, $T_9$ and $T_{10}$ are independently hydrogen or hydroxy protecting group;

$X_1$ is —$OX_6$;

$X_2$ is hydrogen, hydrocarbon, heterosubstituted hydrocarbon, heteroaryl or heterosubstituted heteroaryl;

$X_3$ and $X_4$ are independently hydrogen, hydrocarbon, heterosubstituted hydrocarbon, heteroaryl, heterosubstituted heteroaryl or $RSG_1$;

$X_5$ is —$X_{10}$, —$OX_{10}$, —$SX_{10}$, or —$NX_8X_{10}$;

$X_6$ is hydrogen, hydrocarbon, heterosubstituted hydrocarbon, heteroaryl, heterosubstituted heteroaryl or hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_2$, $Z_4$, $Z_7$, $Z_9$ and $Z_{10}$ are independently hydrocarbon, heterosubstituted hydrocarbon, heteroaryl or heterosubstituted heteroaryl;

$RSG_1$ is an electron-affinic moiety;

$RSG_2$ is —L—$(RSG_1)_n$;

L is a linker comprising a chain of 1 to 30 atoms in the chain, the atoms being selected from the group consisting of C, O, N, S, Si, and P; and n is an integer greater than or equal to 1.

The invention is also directed to pharmaceutical compositions for radiosensitizing tumor cells which contain a radiosensitizing amount of the above described taxanes or a pharmaceutically acceptable salt thereof in admixture with a pharmaceutically acceptable carrier.

The present invention is further directed to a process for radiosensitizing tumor cells. The process comprises administering a radiosensitizing amount of the pharmaceutical composition described above to the tumor cells. Related thereto, a method is also provided for killing tumor cells in a warm-blooded animal which includes the steps of administering to the warm-blooded animal a pharmaceutical composition as described above in an amount effective to radiosensitize the tumor cells, followed by, after a time interval sufficient to enhance radiosensitization of the tumor cells, irradiating the tumor cells with a dose of radiation effective to kill the tumor cells.

Other objects and features will be in part apparent and in part pointed out hereinafter.

DETAILED DESCRIPTION OF THE PREFERRED EMBODIMENTS

Figure 1:
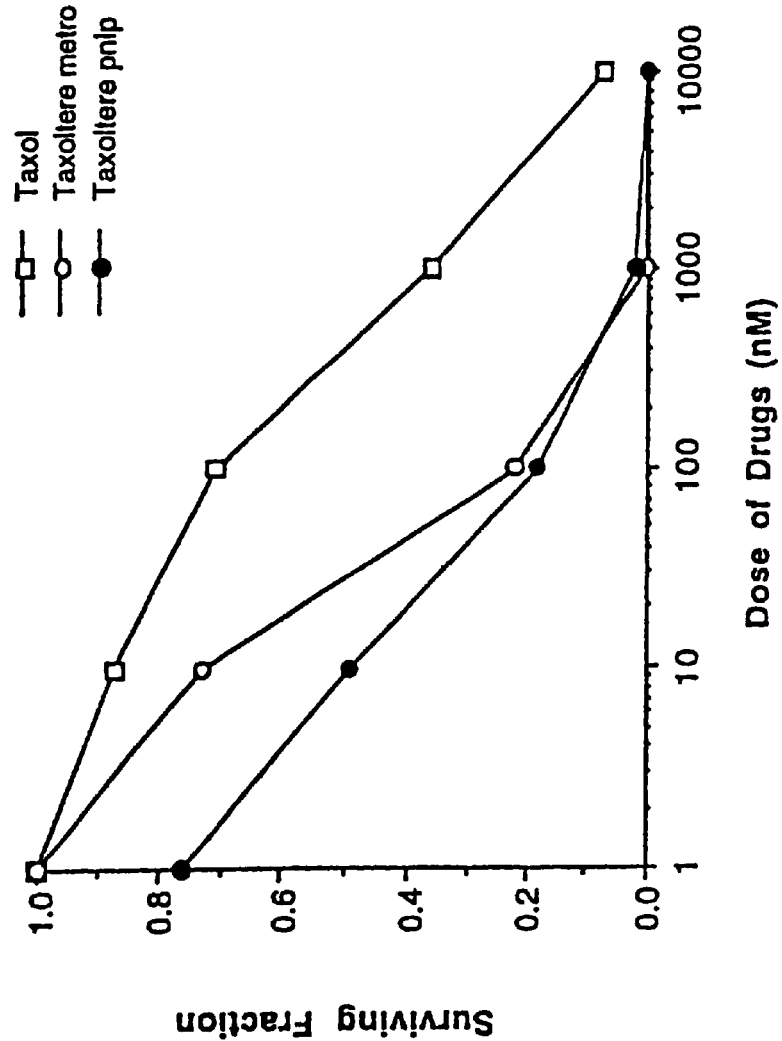
FIG. 1 is a graph depicting in vitro chemotherapeutic activity of taxoltere metro, taxol and taxoltere pnip on CHO cells for the studies set forth in Example 4.1.

Surprisingly, it has been discovered that taxanes containing electron-affinic substituents exhibit significantly greater potency than taxol as a radiosensitizing agent. As a result, such increased potency permits the administration of much lower dosages of these compounds for the same or even greater radiosensitization of tumor cells, allowing for a concomitant reduction in toxic side effects on healthy tissue for any particular dosage level required to effectively radiosensitize the tumor cells.

The radiosensitizing groups or moieties described herein ($RSG_1$ and $RSG_2$) impart electron affinity to the compounds with which they are associated. This novel class of potent radiosensitizers comprise taxanes containing at least one, and optionally two or more electron-affinic moieties. In general, the radiosensitizing moieties contain electron-affinic groups which fall into one of four groups: (i) carbocyclic or heterocyclic aromatic moieties which possess one or more carbonyl, trifluoromethyl, halogen, nitro, sulfonyl, sulfinyl, phosphoryl, oxide or cyano groups, (ii) heterocyclic aromatic moieties containing two or more heteroatoms, (iii) metal complexes, and (iv) organo-metallic groups in which the metal is covalently bonded to carbon.

The carbocyclic or heterocyclic aromatic electron-affinic moieties contain one to three rings with a total of 5 to 15 ring atoms which are selected from the group consisting of C, N, S, O and P. Preferably, the carbocyclic or heterocyclic aromatic electron-affinic moieties contain one to two rings with one ring being presently most preferred. Representative carbocyclic aromatic electron-affinic moieties include phenyl and napthyl groups containing one or more nitro, halogen, carbonyl or sulfonyl substituents, with nitro-substituted phenyl being a preferred carbocyclic aromatic electron-affinic moiety. Representative heterocyclic aromatic electron-affinic moieties include imidazoles, triazoles, pyridines, benzamides, nicotinamides, benzotriazine oxides, furans, thiophenes, oxazoles and thiozoles possessing one or more carbonyl, trifluoromethyl, halogen, nitro, sulfonyl, sulfinyl, phosphoryl, oxide or cyano groups, and preferably at least one nitro group.

Nitroimidazole and nitrotriazole heterocyclic aromatic electron-affinic moieties which may be incorporated into the radiosensitizing agents of the present invention include 2-nitroimidazol-1-yl and 3-nitro-1,2,4-triazol-1-yl and other nitroimidazoles and nitrotriazoles which correspond to the following structures:

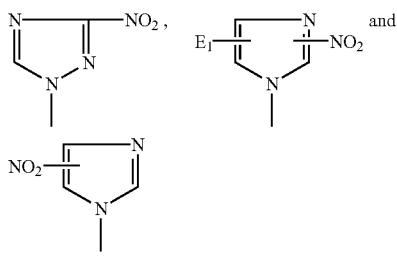

wherein $E_1$ is alkyl or fluoroalkyl. The preparation and use of radiosensitizing agents incorporating these and other nitroimidazoles and nitrotriazoles is described in Suzuki et al., U.S. Pat. Nos. 4,945,102 and 5,064,849; Kagiza et al., U.S. Pat. Nos. 4,927,941, 4,977,273 and 5,304,654; Suto, U.S. Pat. Nos. 4,954,515 and 5,036,096; Suto et al., U.S. Pat. No. 4,797,397; Papadopoulou-Rosenzweig et al., U.S. Pat. No. 5,294,715; Beylin et al., U.S. Pat. No. 5,342,959.

Benzamide and nicotinamide heterocyclic aromatic electron-affinic moieties which may be incorporated into the radiosensitizing agents of the present invention include 5-hydroxynicotinamide;

5-nitronicotinamide;

5-(2,3-dihydroxypropoxy)nicotinamide;

5-aminonicotinamide;

5-(2-methoxyethylamino) nicotinamide;

5-acetamidonicotinamide;

3-hydroxy thiobenzamide;

3-[(2-hydroxyethoxy) acetamido]benzamide;

3-(2,3 dihydroxy-n-propoxy)-4-methoxybenzamide;

3-(2,3 dihydroxy-n-propoxy)-4-methylbenzamide;

4-(2,3 dihydroxy-n-propoxy)-3-methoxybenzamide; and other benzamides and nicotinamides which correspond to the following structures:

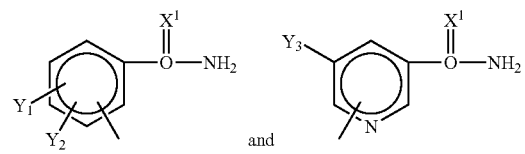

wherein $X^1$ is O or S; $Y_1$ is H, lower alkyl, lower alkoxy, acetoxy, or acetamido; $Y_2$ is —OR, —SR, —NHR, —NO$_2$, —O(CO)R, —NH(CO)R, —O(SO)R, or —O(POR)R; $Y_3$ is H, $Z_1$, —OR, —SR, —NHR, —O(CO)R, —NH(CO)R, —O(SO)R, or —O(POR)R; and R is hydrogen or hydrocarbon which may be optionally substituted and interrupted by an ether (—O—) linkage. The preparation and use of radiosensitizing agents incorporating these and other benzamides and nicotinamides is described in Lee et al., U.S. Pat. Nos. 5,032,617, 5,041,653 and 5,175,287.

Benzotriazine oxide heterocyclic aromatic electron-affinic moieties which may be incorporated into the radiosensitizing agents of the present invention include 3-hydroxy-1,2,4-benzotriazine-1,4-dioxide;

3-amino-7-trifluoro-1,2,4-benzotriazine-1-oxide;

3-amino-7-decyl-1,2,4-benzotriazine-1-oxide;

3-amino-7-carbamyl-1,2,4-benzotriazine-1-oxide;

7-acetyl-3-amino-1,2,4-benzotriazine-1-oxide;

7-chloro-3-hydroxy-1,2,4-benzotriazine-1,4-dioxide;

7-nitro-3-amino-1,2,4-benzotriazine-1,4-dioxide; and other benzotriazine oxides corresponding to the structure:

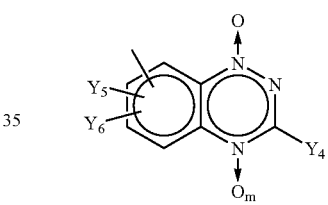

wherein $Y_4$ is H, substituted or unsubstituted lower hydrocarbon, or alkanoyl; m is 0 or 1; and $Y_5$ and $Y_6$ are independently hydrogen, nitro, halogen, morpholino, pyrrolidino, piperidino, substituted or unsubstituted hydrocarbon, —NH$_2$, —NHR', —NR'R'O(CO)R', —NH(CO)R', —O(SO)R', or —O(POR')R' in which R' is substituted or unsubstituted hydrocarbon. The preparation and use of radiosensitizing agents incorporating these and other benzotriazine oxides is described in Lee et al. U.S. Pat. No. 5,175,287.

The metal complex electron-affinic moieties preferably comprise $pt^{2+}$, $Co^{3+}$, $Fe^{2+}$, $Fe^{3+}$, $Pd^{2+}$, $Cu^{2+}$, $Ti^{4+}$, or $Zr^{4+}$ as the metal and generally fall into two subgroups: (a) metal complexes of the carbocyclic and heterocyclic aromatic electron-affinic moieties discussed above, and (b) metal complexes of bidentate ligands comprising nitrogen, carbon or sulfur. In general, metal complexes of bidentate ligands correspond to the formula —BM$^L$X$_K$ wherein B is a bidentate ligand containing nitrogen, carbon or sulfur, M$^L$ is a metal, X is an anionic ligand such as Cl$^-$ or $^-$OAc, and k is 1–4. Exemplary bidentate ligands include:

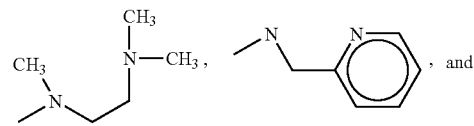

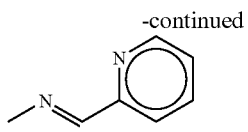

Electron-affinic metal complexes which may be incorporated into the radiosensitizing agents of the present invention include compounds of the formula:

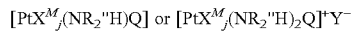

wherein n is 1 or 2, and wherein when n is 2, $X^M$ is a monovalent biologically acceptable anion, and when j is 1, $X^M$ is a divalent biologically acceptable anion; each R" is independently H or alkyl, or both R"s together are a piperidino or morpholino residue; Q is a radiosensitizing ligand selected from a mononitro-substituted imidazole, a mononitro-substituted pyrazole, a mononitro-substituted thiazole and a mononitro-substituted isothiazole; and $Y^-$ is a physiologically acceptable anion. These heterocycles may optionally be substituted by an alkyl, amino substituted alkyl, hydroxy, alkoxy or amino group. In addition, if the heterocycle is pyrazole or imidazole, a ring nitrogen may be substituted by alkyl or alkoxy or hydroxy substituted alkyl and wherein one or two methylenes of the alkyl may be replaced by oxygen. In a preferred embldiment, Q is one of the following:

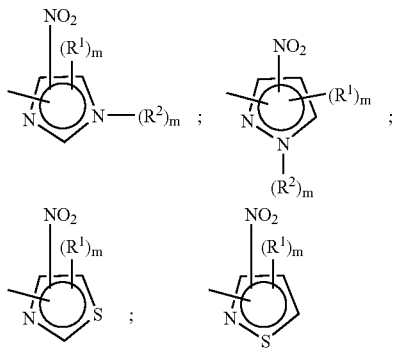

wherein $R^1$ is alkyl optionally containing an amino substituent, $-OR^3$, or $-N(R^3)_2$ wherein $R^3$ is H or lower alkyl; $R^2$ is alkyl or 1–8 carbons substituted by one or more $-OR^3$ and wherein one or two methylenes may be replaced by oxygen and each m is independently 0 or 1. The preparation and use of radiosensitizing agents incorporating these metal complexes is described in Skov et al. U.S. Pat. Nos. 4,921,963 and 5,026,694.

Other electron-affinic metal complexes which may be incorporated into the radiosensitizing agents of the present invention may be made by reacting an organic or inorganic platinum compound such as an alkali metal tetrahaloplatinate or cis-bis(acetonitrile)dichloro-platinum (II) with rhodamine 123 or other (+)-charged rhodamine or the like, for example, a cyanine dye such as 3,3'-diethylthiadicarbocyanine iodide or other (+)-charged cyanine dyes as described in U.S. Pat. No. 5,196,413.

Other electron-affinic metal complexes which may be incorporated into the radiosensitizing agents of the present invention include include Cu(II) compounds selected from compounds having the formula:

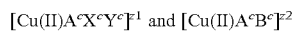

wherein $A^c$ represents a bidentate heteroaromatic ligand containing neutral nitrogen donor atoms; $B^c$ represents a bidentate ligand containing neutral or negatively charged oxygen donor atoms; $X^c$ and $Y^c$ are the same or different neutral or negatively charged monodentate ligands; and $Z^1$ and $Z^2$ represent the charge on the complex. The preparation and use of radiosensitizing agents incorporating these metal complexes is described in Abrams et al. U.S. Pat. No. 5,100,885.

Other electron-affinic metal complexes which may be incorporated into the radiosensitizing agents include Co(III) or Fe(III) compounds a formula corresponding to one of the following formulas:

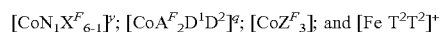

wherein n has a value of 3 or 4; N is an uncharged nitrogen donor atom that is contained within a ligand; $X^F$ represents an anionic ligand; and y represents the charge on the complex; $A^F$ represents a bidentate or tetradentate negative ligand containing N or O donor atoms; $D^1$ and $D^2$ represent the same or different monodentate ligands; q represents a positive or negative charge on the complex; $Z^F$ represents a chelating mononegative negative ligand; $T^1$ and $T^2$, which may be the same or different, represent mono-negative tridentate ligands. The preparation and use of radiosensitizing agents incorporating these metal complexes is described in U.S. Pat. No. 4,727,068.

The organometallic electron-affinic moieties are aliphatic or aromatic mercury radicals. The preparation and use of radiosensitizing agents incorporating mercury containing entities is described in Shenoy et al., Cancer Investigation, 10(6):533–551 (1992) and Bruce et al., Radiation Res., 24:473–481 (1965).

The electron-affinic moieties may be directly attached to one of the carbons of the A, B, or C rings of the taxane or indirectly attached via a linker. The linker comprises a chain of 0 to 30 atoms in the chain, with approximately 10 or less being preferred. The chain atoms are selected from the group consisting of C, O, N, S, Si, and P and are preferably C, N or O. The linker may be linear or cyclic, branched or unbranched, and may contain as substituents, one or more P, C, O, N, S, H, Si or halogen-containing substituents. Exemplary linker substituents include silyls, ethers, thioethers, esters, thioesters, amides, thioamides, amines, alcohol, alkyl, aryl, carbonyl, sulfonyl, phosphoryl, and halogen substituents.

Preferably, the linker comprises a hydrocarbon segment consisting of 1 to 6 carbon atoms. It may additionally comprise a carbonyl, ester, thioester, amide, carbonate, thiocarbonate, carbamate, or ether segment. If a non-hydrocarbon segment is included; the non-hydrocarbon segment preferably comprises one or more ether, carbonate or carbonyl moieties as the non-hydrocarbon segment.

For purposes of illustration, a series of radicals comprising linkers and electronic-affinic moieties falling within the scope of the present invention is set forth as follows:

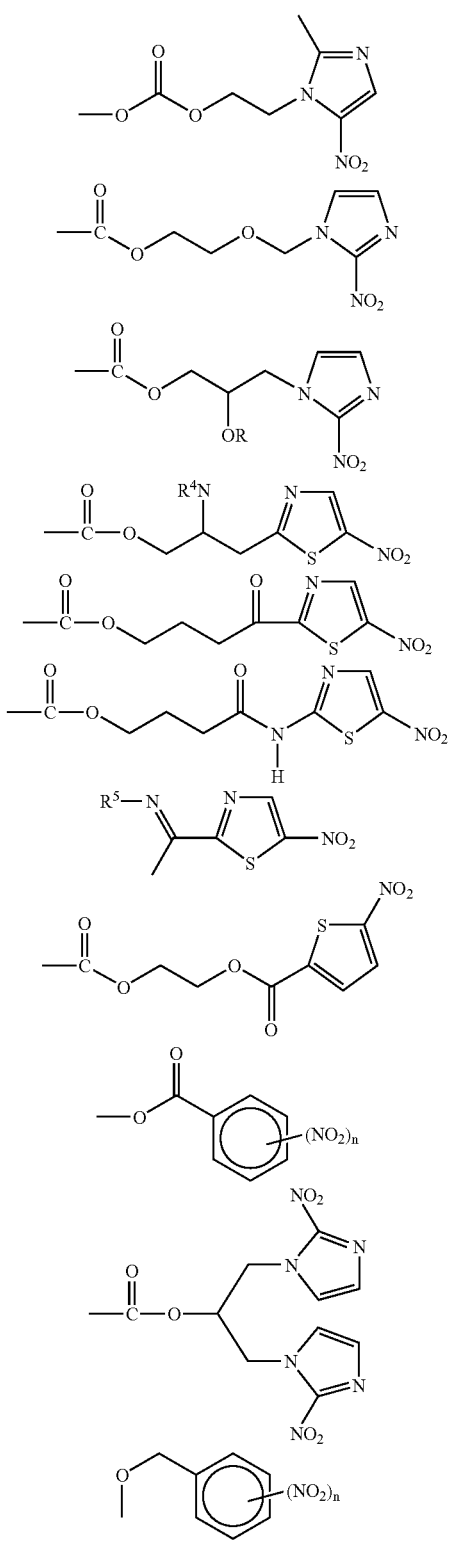

wherein h is 1–3, $R^4$ is H, hydrocarbon or substituted hydrocarbon, and $R^5$ is hydrocarbon or substituted hydrocarbon. In other embodiments, the carbonyl or ester linkage of the above structures may be replaced by thioester or amide linkages. In addition, many of these radicals may serve as ligands for the previously identified metal species.

The radiosensitizing compounds of the present invention are prepared by linking the electron-affinic moiety to the C2, C4, C7, C9, C10, C14, C3', or C5' carbons of a taxane. The starting material may be 10-deacetyl baccatin III, baccatin III, or another naturally occurring taxane such as 14-hydroxy-10-deacetylbaccatin III. Alternatively, the taxane may be synthesized from commodity chemicals as set forth in PCT Patent Application No. WO 95/03265.

Taxanes having C13 side chains which incorporate electron-affinic moieties at C3' and/or C5' may be prepared through the use of β-lactams having the desired substituents and reacting the β-lactam and a C13 metal or ammonium alkoxide of a suitably substituted taxane as more fully described in U.S. Pat. No. 5,430,160. The β-lactams have the following structural formula:

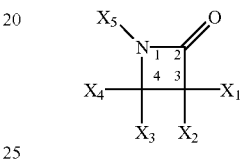

wherein $X_1$ is protected hydroxy, and $X_2$–$X_5$ are as previously defined. Preferably, the alkoxide has the tetracyclic taxane nucleus and corresponds to the structural formula:

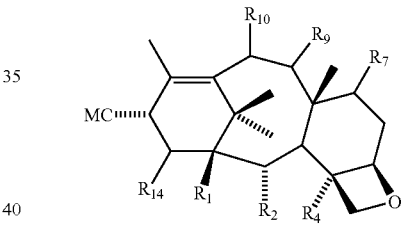

wherein M is a metal or tetraalkylammonium and $R_1$, $R_2$, $R_4$, $R_7$, $R_9$, $R_{10}$, and $R_{14}$ are as previously defined.

The electron-affinic moieties can be attached to the C2, C4, C7, C9, C10, and C14 positions of a taxane by a variety of methods. For purposes of illustration, the attachment method will first be described with respect to the C7 position. As will be described elsewhere herein, however, these same methods can be used for the other positions.

Metronidazole, a well known radiosensitizer, and other electron-affinic moieties can be attached via a carbonate linkage by treating baccatin III 2 with carbonyl diimidazole to produce the 7-carbonylimidazolide 2a, and reacting the product in situ with metronidazole at higher temperature to provide the 7-carbonylmetronidazolide 3. A C13 side chain can then be attached to 7-carbonylmetronidazolide 3 by treating it with lithium hexamethyldisilazide and β-lactam 4, and, after treatment with HF, to yield a taxane which we have named taxoltere metro 5. This reaction sequence is summarized in the following reaction scheme:

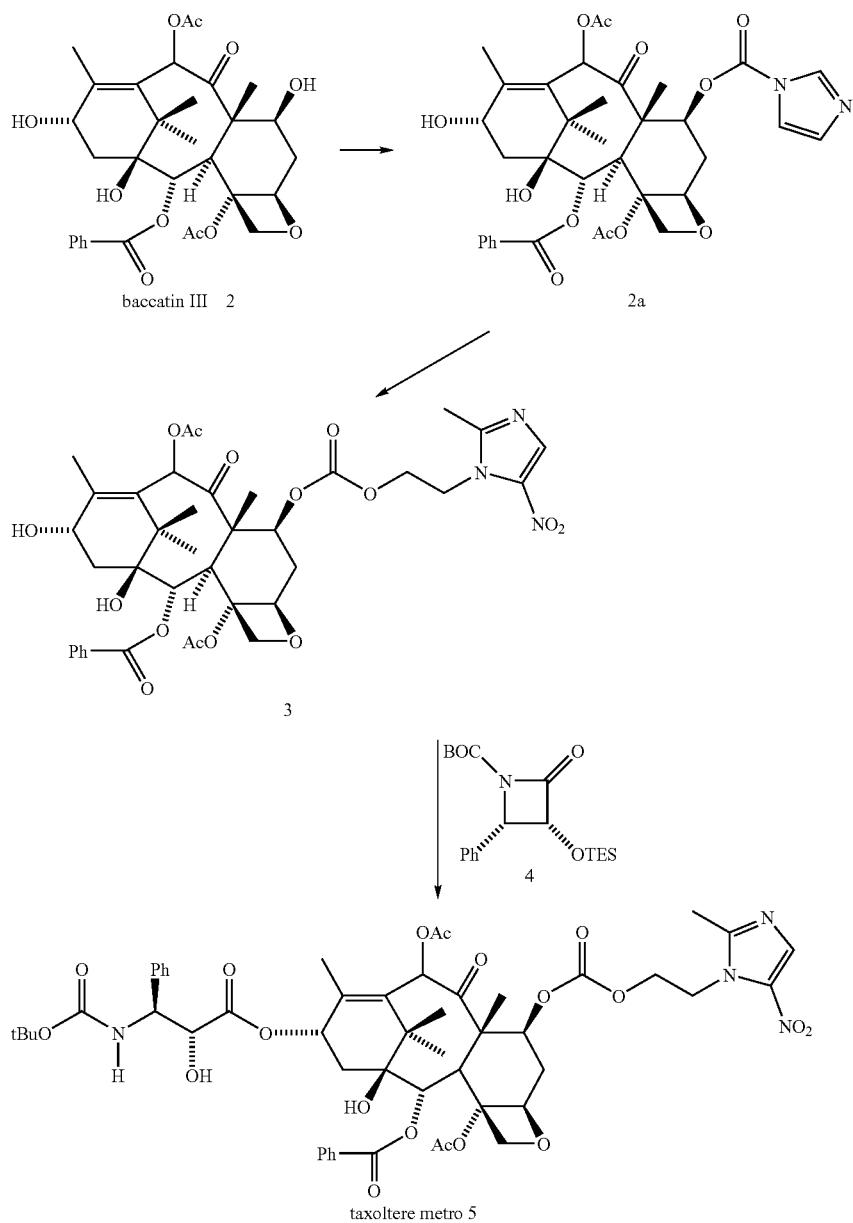

This method can be used for the preparation of a series of similar radiosensitizing taxanes having different radiosensitizing groups. The intermediate 7-carbonylimidazolide 2a reacts smoothly with alcohols to provide the desired radiosensitizing taxanes in which the radiosensitizing group is attached via a carbonate linkage, as in taxoltere metro. For example, alcohols 6 through 9 will react with the carbonylimidazolide substituent of 2a to yield four other taxanes having radiosensitizing groups linked to C7.

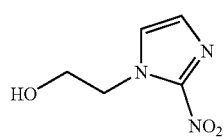
6

-continued

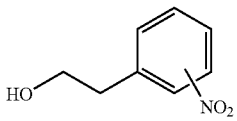
7

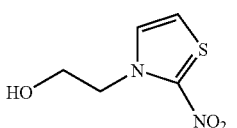
8

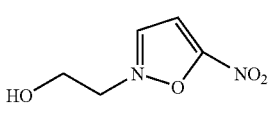
9

Attachment of the radiosensitizing group is then followed by attachment of a side chain at C13 in the same manner as it was accomplished for taxoltere metro.

The attachment of a metal atom or metal complex tethered at the C7 position of the taxane core can be accomplished by reacting an allylchloroformate with a taxane having an available C7 hydroxy group and a protected 2' hydroxy group to produce derivative 10 wherein $X_3$ and $X_5$ are as previously defined and P is a hydroxy protecting group. Hydroboration of the allyl carbonate substituent followed by treatment of the borane with mercuric acetate and sodium chloride and deprotection of the C2' hydroxy group gives the mercury derivative 11, a good radiosensitizer.

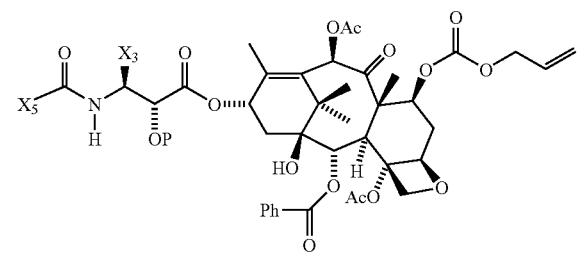

10

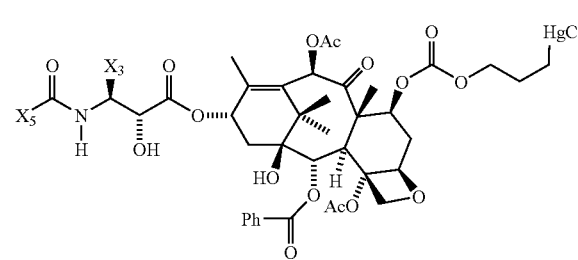

11

The ester analog of 11 can be prepared by the direct acylation of the C7 hydroxyl group of a 2' hydroxy protected taxane with an acid chloride to produce ester 12. Hydroboration of the allyl ester followed by treatment of the borane with mercuric acetate and sodium chloride gives the ester analog of mercury derivative 11.

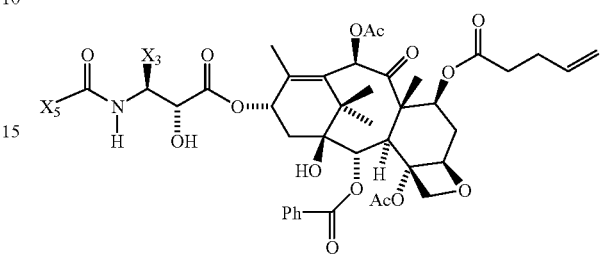

12

Similar chemistry can be used to attach a bidentate ligand to the C7 position, and the metal complex (e.g., platinum) of the bidentate ligand can then be prepared by introducing an appropriate metallic reactant (e.g., $PtCl_2$ or $PtCl_2$ $(SMe_2)_2$). The bidentate ligand can also incorporate an electron-affinic ligand, and the Pt (II) complex of 13 can be made in this way.

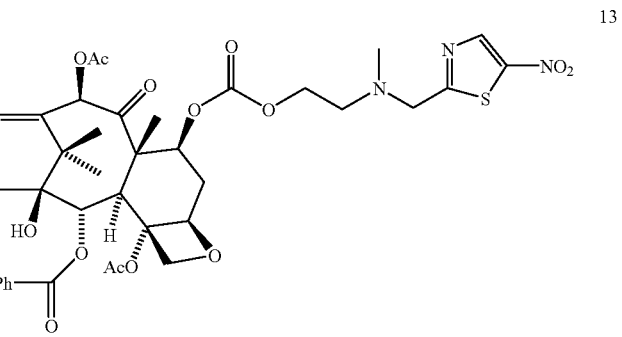

13

The length and nature of the linker between the taxane and the electron-affinic group may be altered. It is possible to prepare analogs in which the electron-affinic group is both closer and further away from the taxane than it is in taxoltere metro. An analog with a longer linker can easily be synthesized by incorporating a dicarboxylic acid diester instead of the carbonate between the taxane and metronidazole, e.g., 14. The p-nitrobenzyl ether 15 and the corresponding p-nitrobenzoate are radiosensitizing taxanes in which the electron-affinic group is very close to the taxane. Alternatively, hydroboration of 10 gives an alcohol, the mesylate of which reacts with, for example, 2-nitro imidazole to provide 16, and the epoxide derived by peracid treatment of 10 reacts with, for example, 2-nitro imidazole to provide 17. Ester analogs of 16 and 17 can be similarly prepared starting from 12.

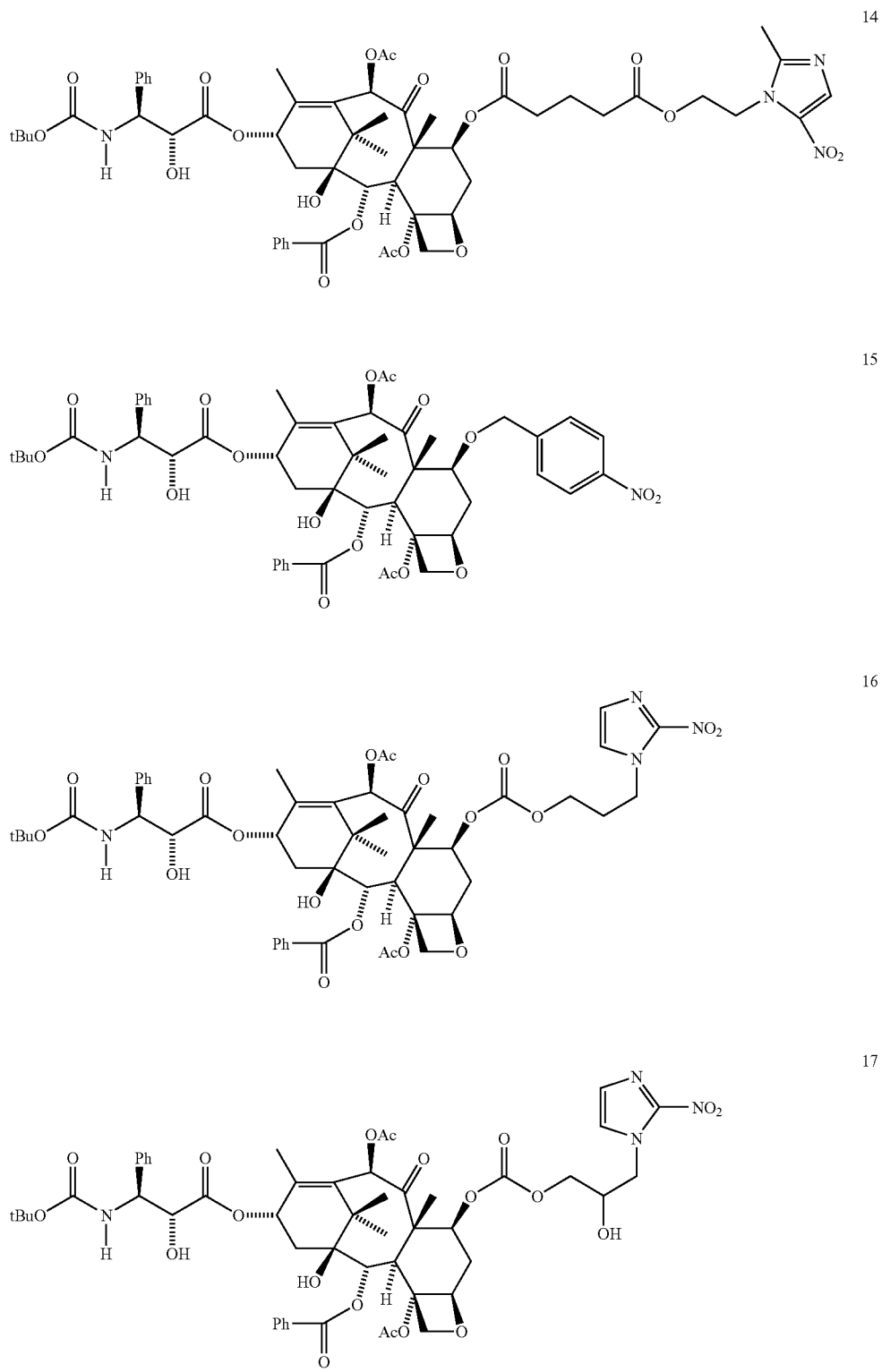
It is also possible to prepare radiosensitizing taxanes having multiple radiosensitizing groups attached to a single linker. For example, reaction of 2-nitro imidazole with glycidyl chloride at somewhat elevated temperature provides alcohol 18, which then reacts with 2a and with β-lactam 4 to give radiosensitizing taxane 19.

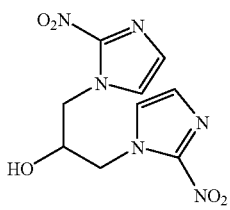

18

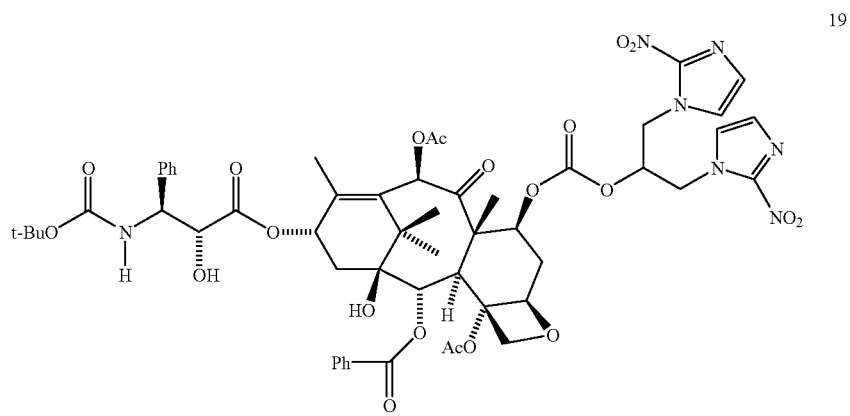

19

Electron-affinic moieties can be attached to the C10 position of a taxane possessing a C10 hydroxy group, such as 10-DAB, by the methods discussed for attaching the electron-affinic moieties to the C7 position. Taxanes having other C10 substituents described herein may be prepared as more fully described in PCT Patent Application WO 94/15599 and other literature references. For example, taxanes having a C10 keto substituent can be prepared by oxidation of 10-desacetyl taxanes. Taxanes which are dihydro substituted at C10 can be prepared by reacting a C10 hydroxy or acyloxy substituted taxane with samarium diiodide. Taxanes having acyloxy substituents other than acetate can be prepared by reacting the C10 hydroxy substituent of 10-deacetyl baccatin III with any standard acylating agent such as anhydrides, acid chlorides, acyl imidazoles or other activated carboxyl derivatives. Taxanes having a C10 carbonate substituent can be prepared by using an analogous chloroformate instead of the acid chloride.

Electron-affinic moieties can be attached to the C9 position of a taxane possessing a C9 hydroxy group by the methods discussed for attaching the electron-affinic moieties to the C7 position. As more fully described in PCT Patent Application WO 94/20088, the C9 the C9 keto substituent of taxol, 10-DAB, baccatin III or can be selectively reduced to yield the corresponding C9 β-hydroxy derivative with a borohydride, preferably tetrabutylammonium borohydride ($Bu_4NBH_4$) or triacetoxy-borohydride. The C9 β-hydroxy derivative can then be protected at C7 with a hydroxy protecting group and the C9 hydroxy group can be acylated following the methods described herein for acylation of the C7 hydroxy group.

Alternatively, reaction of 7-protected-9β-hydroxy derivative with KH causes the acetate group (or other acyloxy group) to migrate from C10 to C9 and the hydroxy group to migrate from C9 to C10, thereby yielding a 10-desacetyl derivative, which can be acylated as described elsewhere herein.

As more fully described in PCT Patent Application WO 94/17050, C7 dihydro and other C7 substituted taxanes can be prepared by tin hydride reduction of the C7 xanthate. C7 fluoro-substituted taxanes can be prepared by treatment of C13-triethylsilyl-protected baccatin III with 2-chloro-1,1,2-trifluorotriethylamine at room temperature in THF solution. Other baccatin derivatives with a free C7 hydroxyl group behave similarly. Alternatively, 7-chloro baccatin III can be prepared by treatment of baccatin III with methanesulfonyl chloride and triethylamine in methylene chloride solution containing an excess of triethylamine hydrochloride. Taxanes having C7 acyloxy substituents can be prepared as set forth in the following reaction scheme. 7,13-protected 10-oxo-derivative is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to C10, migration of the C10 oxo substituent to C9, and migration of the C9 acyloxy substituent to C7.

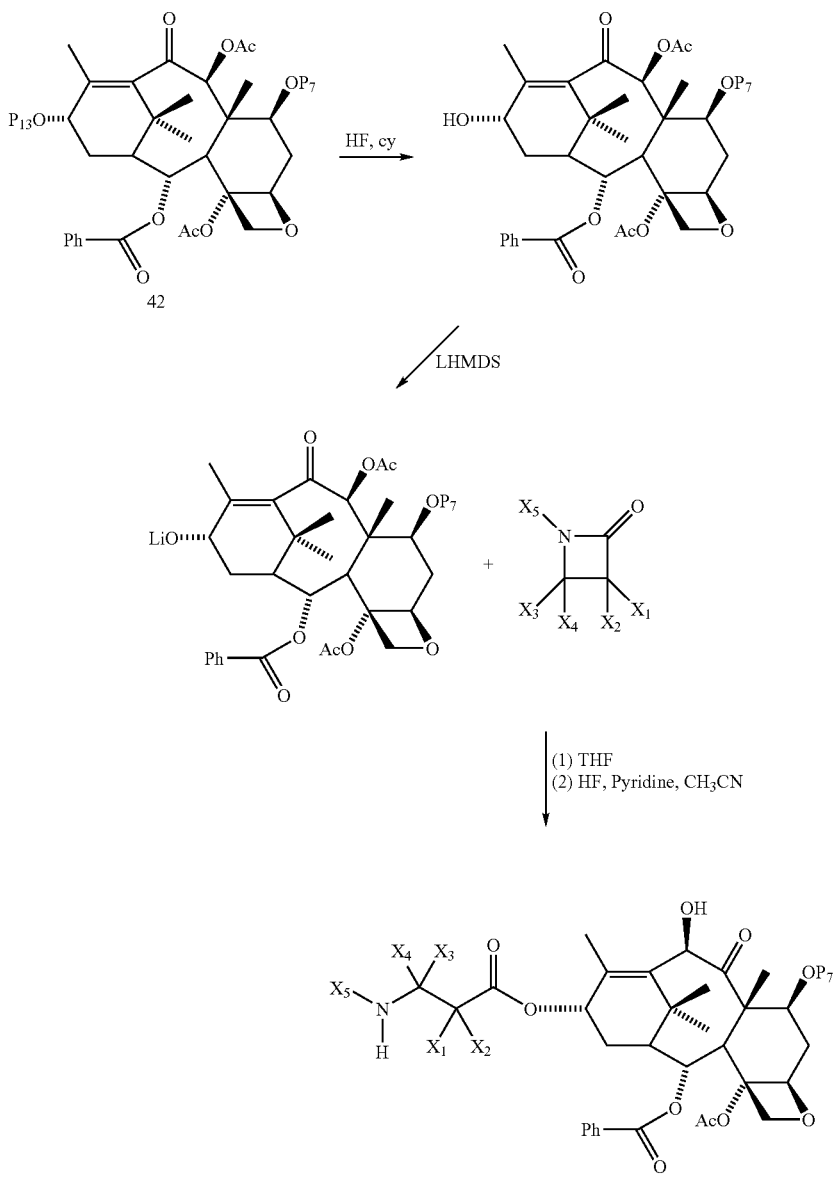

Taxanes having alternative C2 and/or C4 esters or carbonates which optionally may contain an electron-affinic moiety as described elsewhere herein can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride. The corresponding carbonates is can be prepared by substituting a chloroformate for the analogous acid chloride.

Baccatin III and 10-DAB analogs having different substituents at C2 and/or C4 can be prepared as set forth in Reaction Schemes $C_2$-1 to $C_2$-5. To simplify the description, 10-DAB is used as the starting material and only the ester products are shown. It should be understood, however, that other starting materials and reactants may be substituted to yield the other C2 and C4 substituted compounds disclosed herein.

In the Reaction Scheme $C_2$-1, protected 10-DAB 20 is converted to the trial 21 with lithium aluminum hydride. Trial 21 is then converted to the corresponding C4 ester using $Cl_2CO$ in pyridine followed by a nucleophilic agent (e.g., Grignard reagents or alkyllithium reagents) wherein $Z_2$ is as defined elsewhere herein.

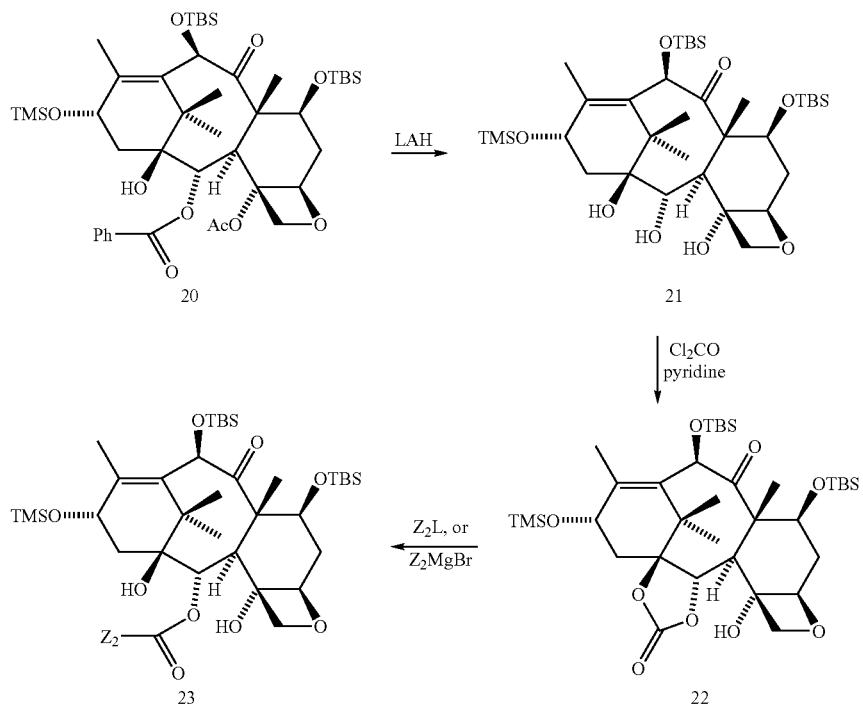

Deprotonation of triol 21 with LDA followed by introduction of an acid chloride selectively gives the C4 ester. For example, when acetyl chloride was used, triol 21 was converted to 1,2 diol 24 as set forth in Reaction Scheme $C_2$-2 wherein $Z_4$ is as defined elsewhere herein.

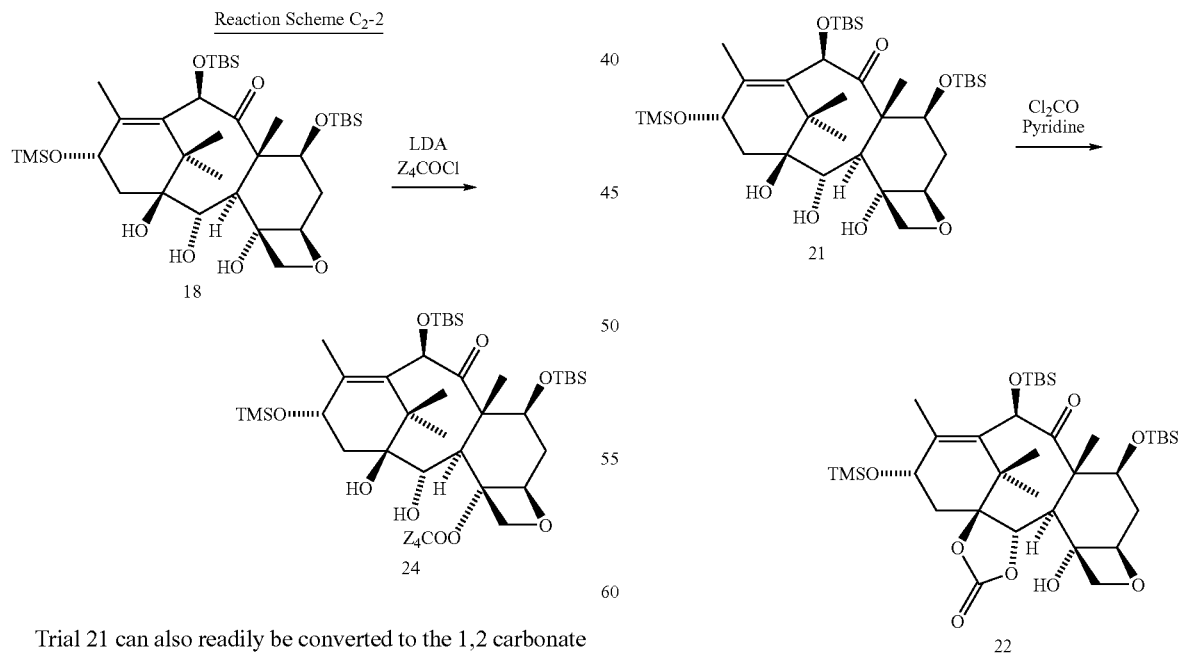

Trial 21 can also readily be converted to the 1,2 carbonate 22. Acetylation of carbonate 22 under vigorous standard conditions provides carbonate 25 as described in Reaction Scheme $C_2$-3; addition of alkyllithiums or Grignard reagents to carbonate 22 provides the C2 ester 24 having a free hydroxyl group at C4 as set forth in Reaction Scheme $C_2$-1.

-continued

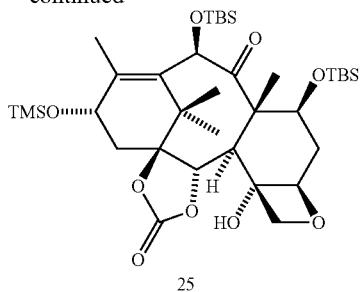

25

As set forth in Reaction Scheme $C_2$-4, other C4 substituents can be provided by reacting carbonate 22 with an acid chloride and a tertiary amine to yield carbonate 26 which is then reacted with alkyllithiums or Grignard reagents to provide 10-DAB derivatives 27 having new substituents at C2 wherein $Z_2$ and $Z_4$ are as defined elsewhere herein.

Alternatively, baccatin III may be used as a starting material and reacted as shown in Reaction Scheme $C_2$-5. After being protected at C7 and C13, baccatin III is reduced with LAH to produce 1,2,4,10 tetraol 29. Tetraol 29 is converted to carbonate 30 using $Cl_2CO$ and pyridine, and carbonate 30 is acylated at C10 with an acid chloride and pyridine to produce carbonate 31 (as shown) or with acetic anhydride and pyridine (not shown). Acetylation of carbonate 31 under vigorous standard conditions provides carbonate 32 which is then reacted with alkyl lithiums to provide the baccatin III derivatives 33 having new substituents at C2 and C10 wherein $Z_2$ and $Z_{10}$ are as defined elsewhere herein.

Reaction Scheme $C_2$-4

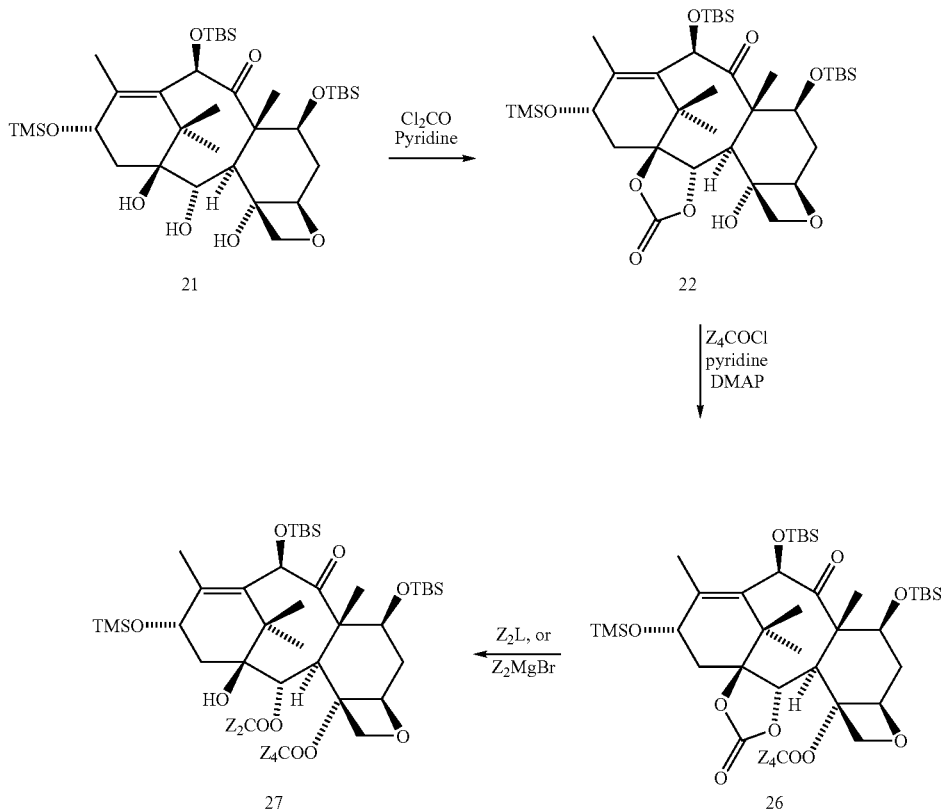

Reaction Scheme C$_2$-5

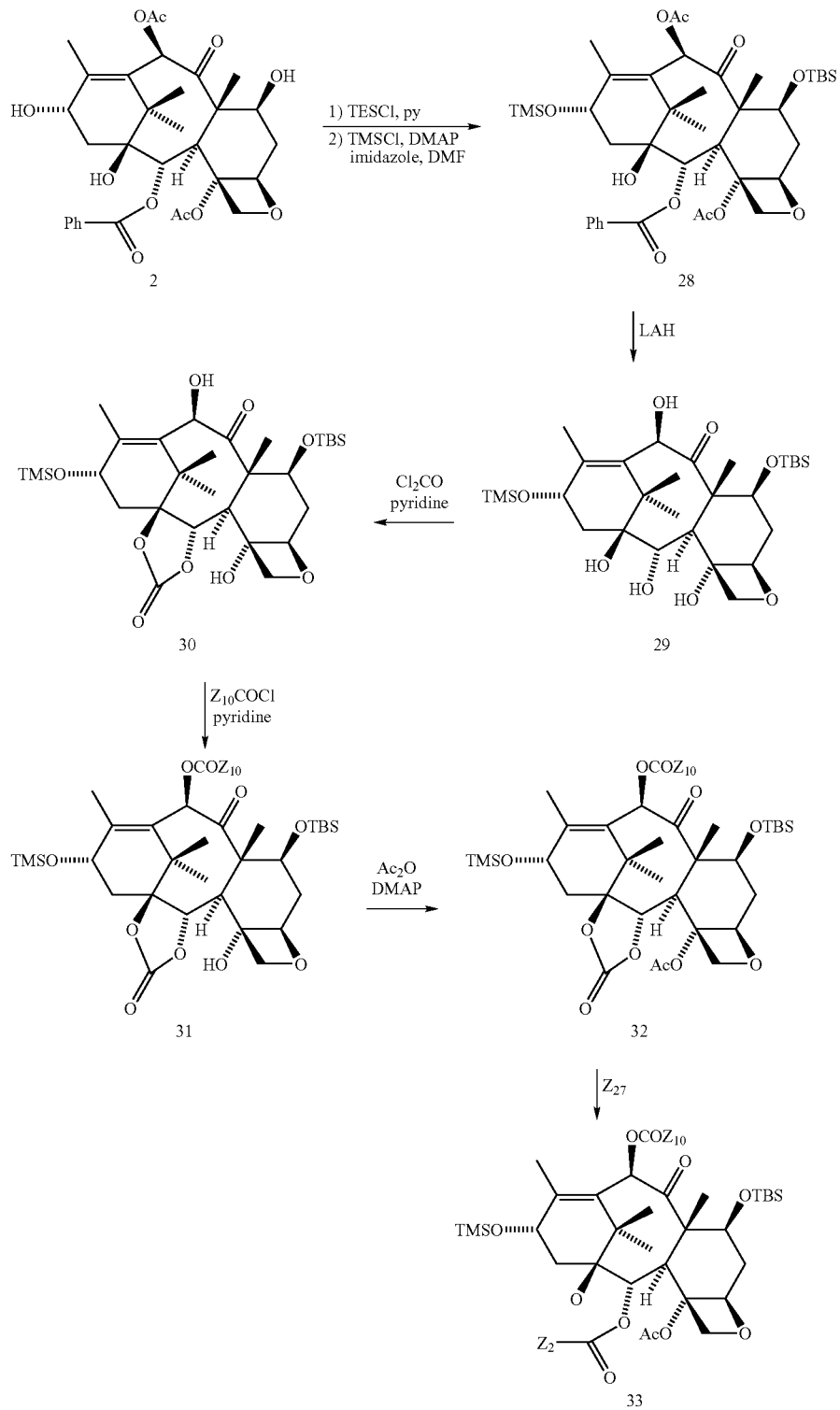

Taxanes having radiosensitizing groups at the C14 position, i.e., the point of attachment of $R_{14}$ as depicted elsewhere herein, may be prepared using the same or similar methods as those described elsewhere herein with respect to attaching radiosensitizing groups to the C7 position of the taxane. The starting material for these compounds may be, for example, a hydroxylated taxane (14-hydroxy-10-deacetylbaccatin III) which has been discovered in an extract of yew needles (C&EN, p 36–37, Apr. 12, 1993). Derivatives of this hydroxylated taxane having the various C2, C4, C7, C9, C10, C3' and C5' functional groups described above may also be prepared by using this hydroxylated taxane. In addition, the C14 hydroxy group together with the C1 hydroxy group of 10-DAB can be converted to a 1,2-carbonate as described in C&EN or it may be converted to a variety of esters or other functional groups as otherwise described herein in connection with the C2, C4, C9 and C10 substituents.

The taxane radiosensitizers of the present invention can be combined with various excipient vehicles and/or adjuvants well known in this art which serve as pharmaceutically acceptable carriers to permit drug administration in the form of, e.g., injections, suspensions, emulsions, tablets, capsules, and ointments. These pharmaceutical compositions, containing a radiosensitizing amount of the described substituted diamine compounds, may be administered by any acceptable means which results in the radiosensitization of tumor cells. For warm-blooded animals, and in particular, for humans undergoing radiotherapy treatment, administration can be oral, parenteral, subcutaneous, intravenous, intramuscular and/or intraperitoneal. To destroy tumor cells, the pharmaceutical composition containing the radiosensitizing diamines are administered in an amount effective to radiosensitize the tumor cells (in the range of 1 to 100 mg/kg for humans). The specific dosage administered will be dependent upon such factors as the general health and physical condition of the patient as well as his age and weight, the stage of the patient's disease condition, and the existence of any concurrent treatments.

After administration of the radiosensitizing composition to the tumor cells and the passage of a time interval sufficient to enhance radiosensitization of the tumor cells, the tumor cells are irradiated with a dose of radiation effective to destroy the tumor cells. Generally, the patient will receive a total radiation dosage of about 60 to 76 Gy over seven to eight weeks, each individual radiation dose to be given within approximately 1 to 4 hours after administration of the radiosensitizer. Such sequences of radiosensitization treatments and irradiation are repeated as needed to abate and, optimally, reduce or eliminate, the spread of the malignancy.

Definitions

The "hydrocarbon" moieties described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like. They may be substituted with aliphatic or cyclic hydrocarbon radicals or heterosubstituted with the various substituents defined herein.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbon radicals or hetero-substituted with the various substituents defined herein.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbon radicals or hetero-substituted with the various substituents defined herein.

The aryl moieties described herein contain from 6 to 20 carbon atoms and include phenyl. They may be hydrocarbon or heterosubstituted with the various substituents defined herein. Phenyl is the more preferred aryl.

The heteroaryl moieties described are heterocyclic compounds or radicals which are analogous to aromatic compounds or radicals and which contain a total of 5 to 20 atoms, usually 5 or 6 ring atoms, and at least one atom other than carbon, such as furyl, thienyl, pyridyl and the like. The heteroaryl moieties may be substituted with hydrocarbon, heterosubstituted hydrocarbon or hetero-atom containing substituents with the hetero-atoms being selected from the group consisting of nitrogen, oxygen, silicon, phosphorous, boron, sulfur, and halogens. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The heterosubstituted hydrocarbon moieties described herein are hydrocarbon moieties which are substituted with at least one atom other than carbon, including moieties in which a carbon chain atom is substituted with a hetero atom such as nitrogen, oxygen, silicon, phosphorous, boron, sulfur, or a halogen atom. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The acyl moieties described herein contain hydrocarbon, substituted hydrocarbon or heteroaryl moieties.

The alkoxycarbonyloxy moieties described herein comprise lower hydrocarbon or substituted hydrocarbon moieties.

The term "taxane" as used herein, denotes compounds containing the A, B and C rings (with numbering of the ring positions shown herein):

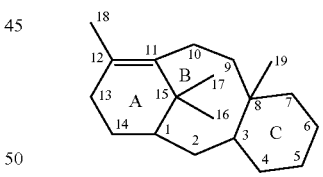

As used herein "Ac" means acetyl; "AIBN" means azo-(bis)-isobutyronitrile; "Ar" means aryl; "BMDA" means BrMgNiPr$_2$; "BOC" means butyloxycarbonyl; "BOM" means benzyloxymethyl; "10-DAB" means 10-desacetylbaccatin III; "DBU" means diazabicycloundecane; "DMAP" means p-dimethylamino pyridine; "DDQ" means dicyano-dichloroquinone; "DMF" means dimethylformamide; "Et" means ethyl; "FAR" means 2-chloro-1,1, 2-trifluoro-triethylamine; "iPr" means isopropyl; "LAH" means lithium aluminum hydride; "LDA" means lithium diisopropylamide; "LHMDS" means lithium hexamethyldisilazide; "LTMP" means lithium tetramethylpiperidide; "mCPBA" means metachloro-perbenzoic acid; "Me" means methyl; "MOP" means 2-methoxy-2-propyl; "Ms" means CH$_3$SO$_2$—; "Ph" means phenyl; "protected hydroxy" means —OP or —OT wherein P or T is a hydroxy protecting group; "py" means pyridine; "R" means lower alkyl unless otherwise defined; "Red-Al" means sodium bis(2-methoxyethoxy) aluminum hydride; "Swern" means $(COCl)_2$, $Et_3N$; "TASF" means tris(diethylamino)-sulfoniumdifluorotrimethyl-silicate; "TBAF" means tetrabutylammonium fluoride; "tBu" and "t-Bu" means tert-butyl; "TBS" means $Me_2$t-BuSi-; "TES" means triethylsilyl; "Tf" means —$SO_2CF_3$; "TMS" means trimethyl-silyl; "TPAP" means tetrapropylammonium perruthenate; and "Ts" means toluenesulfonyl. "Hydroxy protecting group" includes, but is not limited to, acetals having two to ten carbons, ketals having two to ten carbons, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-tri-chloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl protecting groups may be found in "Protective Groups in Organic Synthesis" by T. W. Greene, John Wiley and Sons, 1981.

To further illustrate and explain the invention, several examples are presented below.

EXAMPLE 1

Preparation of 7-(metronidazoleoxycarbonyl) baccatin III hn-4-99-4d-2-1

To a solution of baccatin III (100 mg, 0.170 mmol) in anhydrous 1,2-dichloroethane (1 mL) under nitrogen was added 1,1'-carbonyldiimidazole (55 mg, 0.40 mmol) and the reaction mixture was warmed up to 60° C. and stirred at that temperature for 10 h at which time the reaction was complete. Metronidazole (292 mg, 1.72 mmol) was added (neat) and the mixture was refluxed under nitrogen atmosphere. The progress of the reaction was monitored by NMR. When the reaction was complete (approximately three days) the mixture was diluted with ethyl acetate and washed with saturated sodium bicarbonate, brine. The organic layer was separated, dried and concentrated. The crude mixture was purified by flash chromatography to give 81 mg (70%) of the 7-(metroronidazole-oxycarbonyl)baccatin III: mp. 220–223° C.; $[\alpha]_{Hg}^{25}$=–44.9

$^1$H NMR (CDCl$_3$, 500 MHz) δ8.10 (d, J=7.1 Hz, 2H, benzoate), 7.96 (s, 1H, imidazole), 7.62–7.46 (m, 3H, benzoate), 6.28 (s, 1H, H10), 5.61 (d, J=6.8 Hz, 1H, H2β), 5.49 (m, 1H, H7) 4.96 (d, J=8.2 Hz, 1H, H5), 4.85 (br s, 1H, H$^{13}$) 4.62–4.43 (m, 4H, methylenes), 4.31 (d, J=8.5 Hz, 1H, H20α), 4.13 (d, J=7.5 Hz, 1H, H20β), 3.99 (d, J=6.8 Hz, 1H, H3), 2.59 (m, 1H, H6α), 2.50 (s, 3H, CH3-imidazole), 2.29 (m, 5H, 4Ac, H14's), 2.13 (s, 3H, 10Ac), 2.10 (br s, 3H, Me18) 2.06 (d, J=5 Hz, 1H, 13OH), 1.9 (m, 1H, H6β), 1.77 (s, 3H, Me19), 1.59 (s, 1H, 1OH), 1.17 (s, 3H, Me17), 1.08 (s, 3H, Me16).

EXAMPLE 2

Preparation of N-debenzoyl-N-(t-butylcarbamoyl)-7-(metronidazoleoxycarbonyl) taxol. (Taxoltere metro)

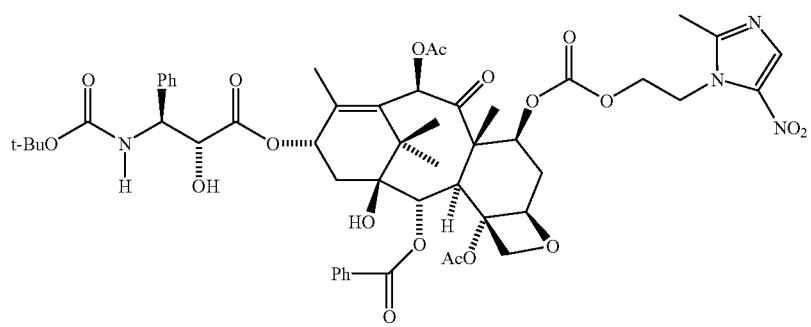

hn-4-119-2

To a solution of 7-(metronidazoleoxycarbonyl) baccatin III (31 mg, 0.039 mmol) in 0.3 mL of THF at −45° C. was added dropwise 0.048 mL of a 1.00 M solution of lithium bis(trimethylsilyl)amide in THF. After 0.5 h at −45° C., a solution of cis-1-(t-butoxycarbonyl)-3-triethylsilyloxy-4-phenylazetidin-2-one (75 mg, 0.20 mmol) in 0.3 mL of THF was added dropwise to the mixture. The solution was warmed to 0° C. and kept at that temperature for 1 h before 0.2 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 45.0 mg of a mixture containing (2'R,3'S) -2'-triethylsilyl-N-debenzoyl-N-(t-butylcarbamoyl)-7-(metronidazoleoxycarbonyl) taxol and a small amount of the (2'S, 3'R) isomer.

To a solution of 45.0 mg of the mixture obtained from the previous reaction in 1.5 mL of acetonitrile and 0.6 mL of pyridine at 0° C. was added 0.2 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 40.8 mg of material which was purified by plug filtration and recrystallization from methanol/water to give 32.3 mg (79%) of N-debenzoyl-N-(t-butylcarbamoyl)-7-(metronidazoleoxy-carbonyl) taxol. m.p. 169–172° C.; $[\alpha]_{Na}^{25}$ −52° C. (0.0035, CHCl$_3$).

$^1$H NMR (CDCl$_3$, 300 MHz) δ8.10 (d, J=7.1 Hz, 2H, benzoate), 7.96 (s, 1H, imidazole), 7.62–7.26 (m, 8H, benzoate,3'phenyl), 6.25 (s, 1H, H10), 6.18 (dd, J=8.8, 8.8 Hz, 1H, H13), 5.65 (d, J=7.1 Hz, 1H, H2β), 5.44–5.21 (m, 3H, NH, H3', H2'), 4.91 (d, J=9.9 Hz, 1H, H5), 4.62 (m, 4H, methylenes), 4.44 (m, 1H, H7), 4.31 (d, J=8.2 Hz, 1H, H20α), 4.15 (d, J=8.2 Hz, 1H, H20β), 3.90 (d, J=7.1 Hz, 1H, H3), 3.35 (d, J-5.5 Hz, 1H, 2'OH), 2.59 (m, 1H, H6α), 2.49 (s, 3H, CH3-imidazole), 2.36 (s, 3H, 4Ac), 2.31 (m, 2H, H14), 2.13 (s, 3H, 10Ac), 1.95 (m, 1H, H6β), 1.88 (br s, 3H, Me18), 1.77 (s, 3H, Me19), 1.70 (s, 1H, 1OH), 1.34 (s, 9H, t-butyl), 1.23 (s, 3H, Me17), 1.15 (s, 3H, Me16).

EXAMPLE 3

Preparation of N-debenzoyl-N-(t-butylcarbamoyl)-3'-desphenyl-31'-(4-nitrophenyl) taxol. (Taxoltere p-nip)

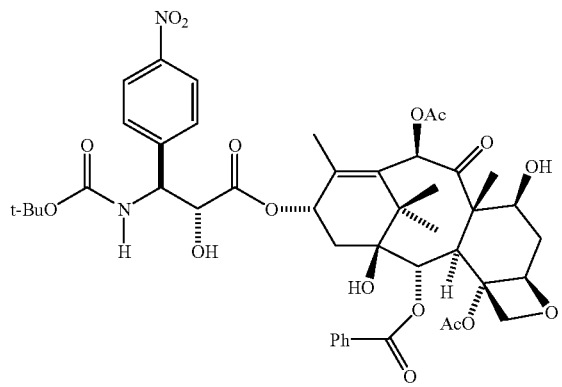

hn-2-66-3

To a solution of 7-triethylsilyl baccatin III (120 mg, 0.171 mmol) in 1.2 mL of THF at −45° C. was added dropwise 0.104 mL of a 1.63 M solution of nBuLi in hexane. After 0.5 h at −45° C., a solution of cis-1-(t-butoxycarbonyl)-3-triethylsilyloxy-4-(4-nitrophenyl)azetidin-2-one (361 mg, 0.885 mmol) in 1.2 mL of THF was added dropwise to the mixture. The solution was warmed to 0° C. and kept at that temperature for 1 h before 1 mL of a 10% solution of ACOH in THF was added. The mixture was partitioned between saturated aqueous NaHCO₃ and 60/40 ethyl acetate/hexane. Evaporation of the organic layer gave a residue which was purified by filtration through silica gel to give 192 mg of a mixture containing (2'R,3'S)-2',7-(bis)triethylsilyl-N-debenzoyl-N-(t-butylcarbamoyl)-3'-desphenyl-3'-(4-nitrophenyl) taxol and a very small amount of the (2'S,3'R) isomer.

To a solution of 192 mg of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 153 mg of material which was purified by flash chromatography to give 140 mg (91%) of N-debenzoyl-N-(t-butylcarbamoyl)-3'-desphenyl-3'-(4-nitrophenyl) taxol, which was recrystallized from methanol/water. m.p. 172–173° C.; $[\alpha]^{25}_{Na}$ −54° C. (c 0.0046, CHCl₃)

EXAMPLE 4

Figure 2:
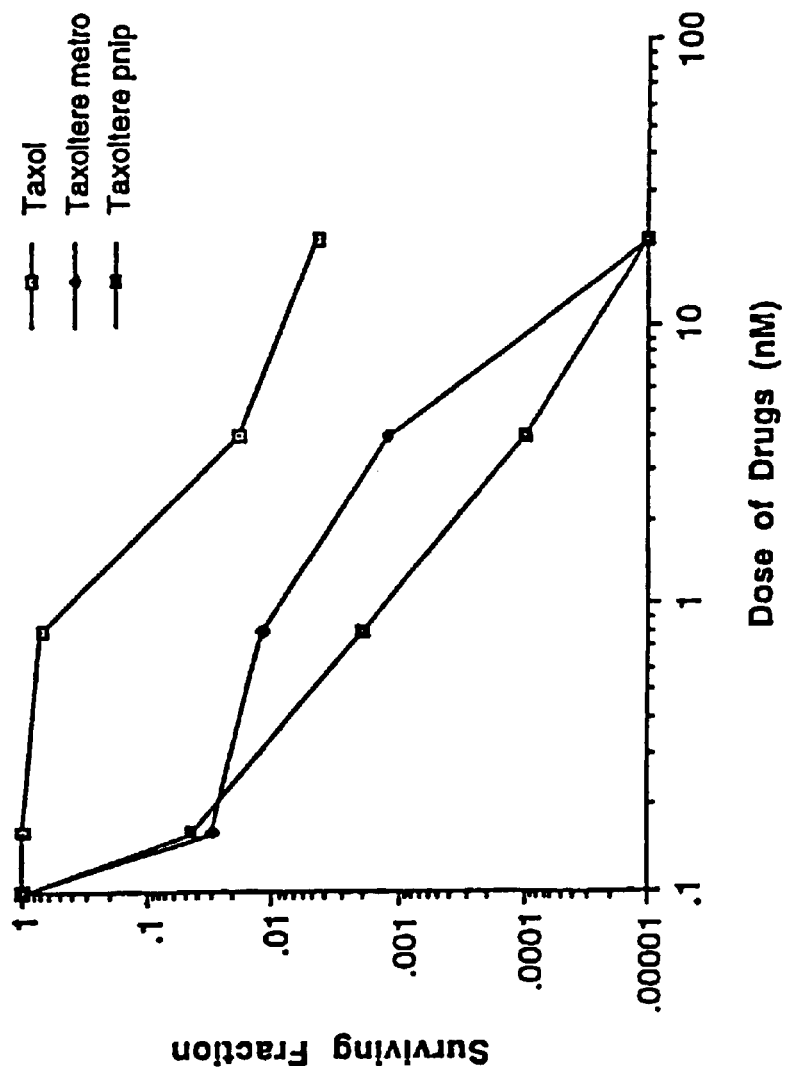
FIG. 2 is a graph depicting in vitro chemotherapeutic activity of taxoltere, taxol and taxoltere pnip on HCT 116 cells for the studies set forth in Example 4.1.

Biological Studies of Taxoltere Metro and Taxoltere p-nip 4.1. In vitro chemotherapeutic activity. Chinese hamster ovary (CHO) and human colon carcinoma (HCT-116) cells were treated with different concentrations of taxol, taxoltere metro, or taxoltere p-nip at 37° C. for 24 hours. Cell survival was evaluated by the colony forming assay. As shown in FIGS. 1 and 2, both taxoltere metro and taxoltere p-nip are much more efficient than taxol in killing CHO and HCT-116 cells. At the 50% survival level, taxoltere metro is about 15 times, and taxoltere p-nip is about 45 times, more effective than taxol in killing CHO cells; measured at the 1% survival level, taxoltere metro is about 10 times, and taxoltere p-nip is about 30 times, more effective than taxol in killing HCT-116 cells. As illustrated in FIGS. 1 and 2, both taxoltere metro and taxoltere p-nip exhibit significantly stronger ability than taxol to kill both types of cells at every drug dose point.

Figure 3:
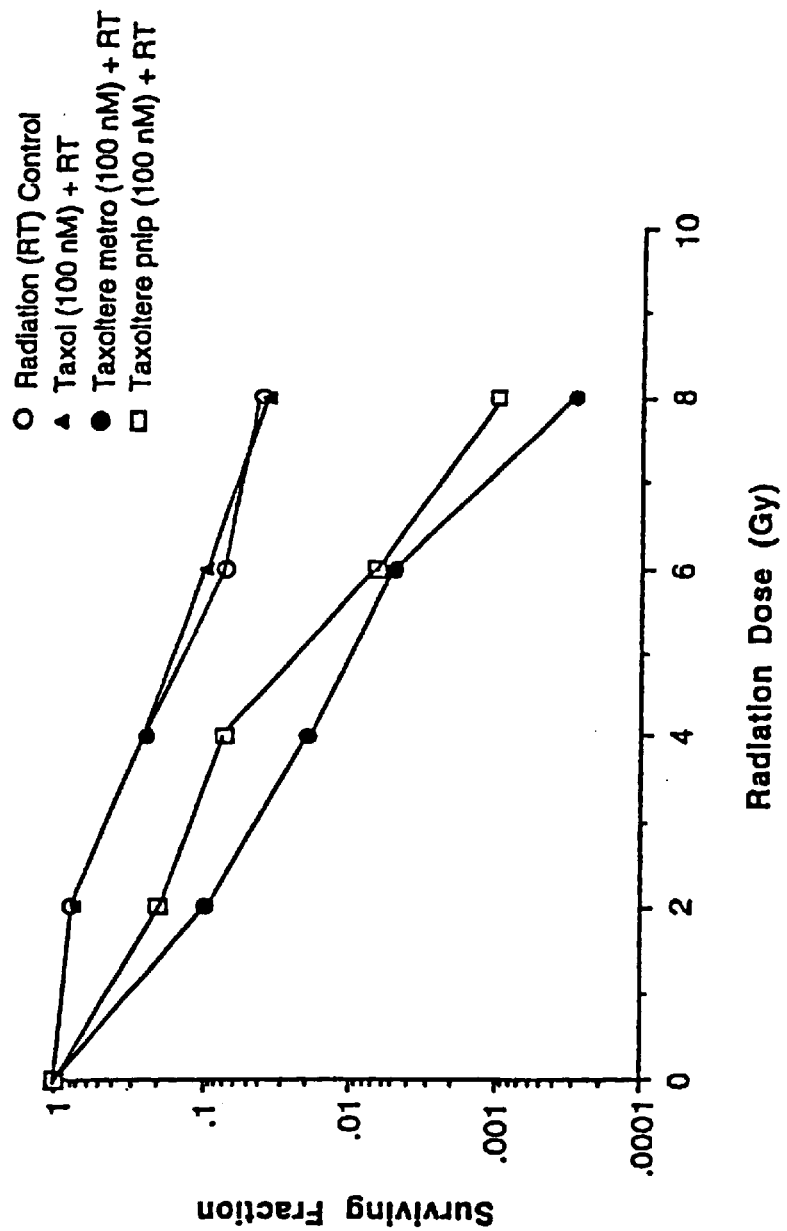
FIG. 3 is a graph depicting in vitro chemotherapeutic radiosensitization of taxoltere metro and taxoltere pnip on CHO cells for the studies set forth in Example 4.2.
Figure 4:
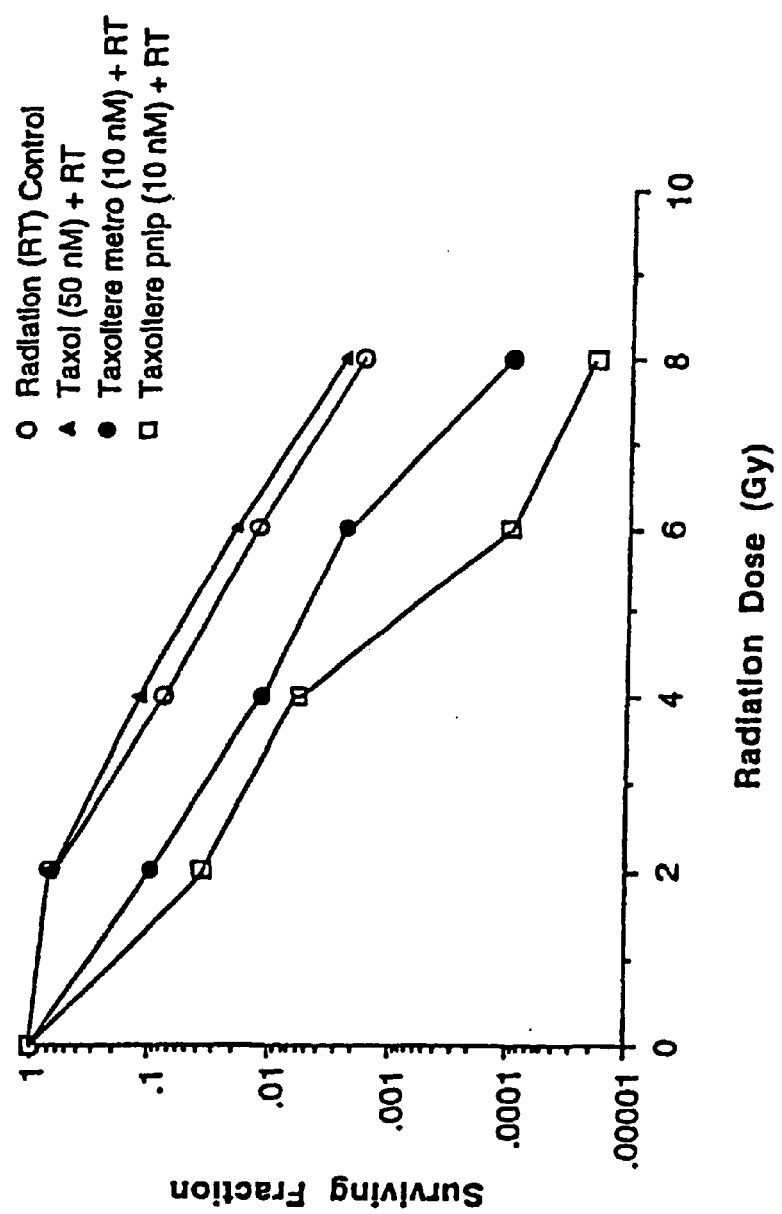
FIG. 4 is a graph depicting in vitro chemotherapeutic radiosensitization of taxoltere metro and taxoltere pnip on HCT 116 cells for the studies set forth in Example 4.2.

4.2. In vitro chemotherapeutic radiosensitization. These studies were carried out as above except that cells were irradiated (General Electric Maxitron 300 at 250 kvp and 20 mA (HVL 20 mm Al filter; dose rate of 2 Gy/min) after two hours incubation. FIGS. 3 and 4 show the results of experiments in which cells were subjected to different radiation doses in the presence or absence of drugs. Both taxoltere metro and taxoltere p-nip strongly radiosensitize both CHO and HCT-116 cells, although taxol does not. For CHO cells, the sensitizer enhancement ratio (SER) is 2.3 for 100 nM taxoltere metro and 1.6 for taxoltere p-nip. For HCT-116 cells, taxoltere metro shows a SER of 1.2 at the (low) dose of 10 nM, and taxoltere p-nip has a SER of 1.5. At each radiation dose point, there is a significantly enhanced decrease in the surviving fraction for the taxoltere metro and taxoltere p-nip treated groups, but not for the taxol treated groups. HCT-116 cells are more sensitive to both taxoltere metro and taxoltere p-nip than CHO cells, hence lower concentrations of the drugs are required for a significant enhancement of radiation induced cell killing.

4.3. In vivo drug toxicity. Acute toxicity experiments were conducted on C3H/HeJ mice. The $LD_{50}$ (lethal dose to 50% of animals) values were determined by standard procedures described by Chan and Hayes (Chan, P. K. and Hayes, A. W. Principles and Methods for acute toxicity and eye irritancy. In Hayes, A. W., ed. Principles and Methods of Toxicity. 2nd Ed., New York, N.Y., Raven Press; 1989: 169220). The $LD_{50/5}$ for i.p. taxoltere metro is 249.67 mg/kg, compared with 140.97 mg/kg for i.p. taxol. At high drug dose levels, the death of mice in the taxol treated groups occurred sooner than the death of mice in the taxoltere metro treated groups. Severe toxic symptoms such as the constriction of pupils and the contraction of erectile tissue of hair follicles (resulting in rough hair) were observed 24 hours after drug administration in the taxol treated groups, but not in the taxoltere metro treated groups. Obviously, the acute toxicity of taxoltere metro is significantly lower than that of taxol. The $LD_{50/5}$ values are 79.13 mg/kg for i.p. administration of taxoltere p-nip and 134.16 mg/kg for i.v. administration of taxoltere p-nip. The data strongly demonstrate that taxoltere p-nip is significantly less toxic when administered i.v. than it is when administered i.p.

Figure 5:
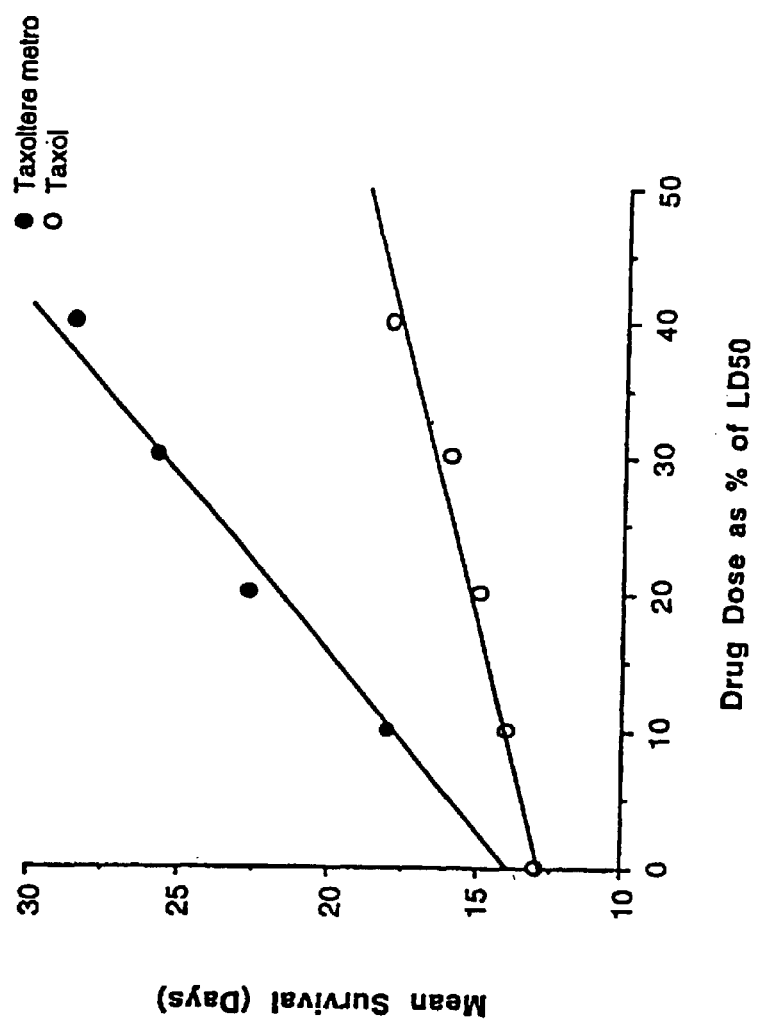
FIG. 5 is a graph depicting in vivo dose-response curves for taxoltere metro and taxol for the studies set forth in Example 4.4.
Figure 6:
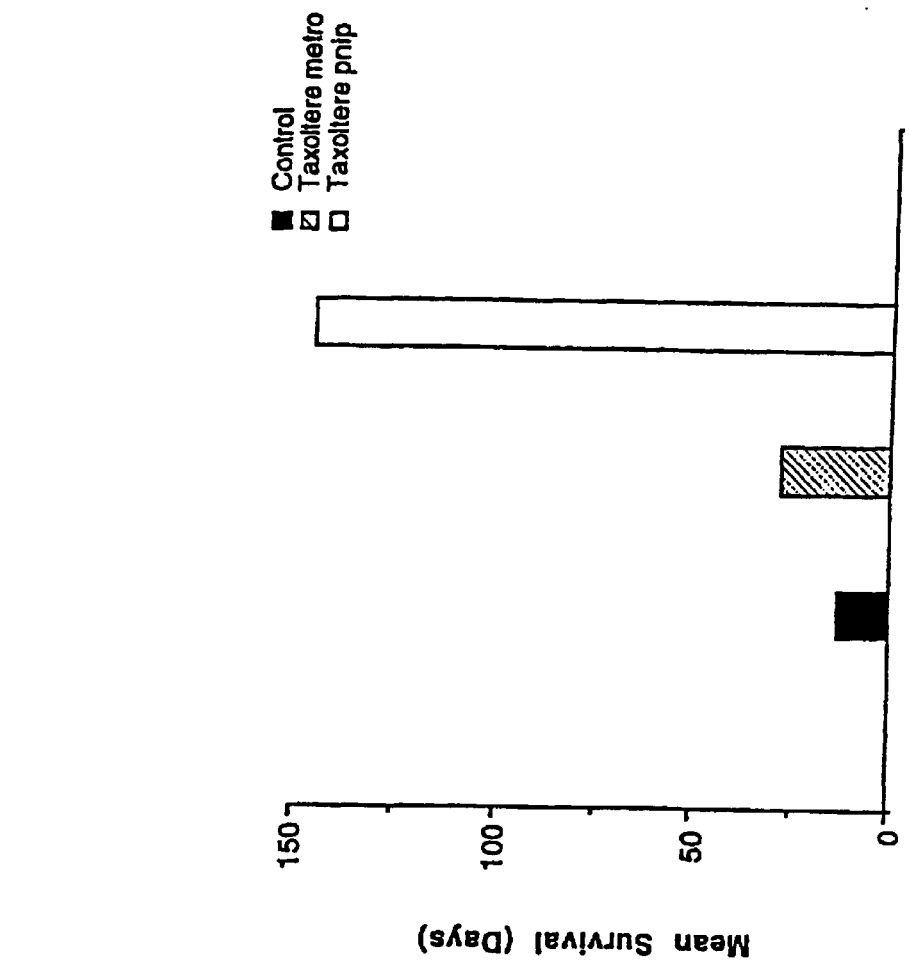
FIG. 6 is a graph depicting in vivo chemotherapeutic activity of taxoltere metro and taxoltere pnip at 40% of $LD_{50}$ for the studies set forth in Example 4.4.

4.4. In vivo chemotherapeutic activity. Taxol, taxoltere metro, and taxoltere p-nip were administered at equitoxic doses using C3H/Hej mice bearing a mouse mammary adenocarcinoma (MTG-B) in the right flank. As illustrated in FIG. 5, taxol-metro is much more effective than taxol in increasing the life span of mammary tumor-bearing mice. The survival time for control mice was 13 days. At 40% of the $LD_{50/5}$ dose, taxol increased the survival time by 31% to 17 days, and taxoltere metro increased the survival time by 123% to 29 days. Taxoltere p-nip (FIG. 6) is substantially more potent, increasing the life span by 1015% to 145 days (dose-response data not shown because only a single dose (40% of $LD_{50/5}$) was studied). Thus, under equitoxic conditions, taxoltere metro was 4 times, and taxoltere p-nip was 33 times, more effective than taxol.

Figure 7:
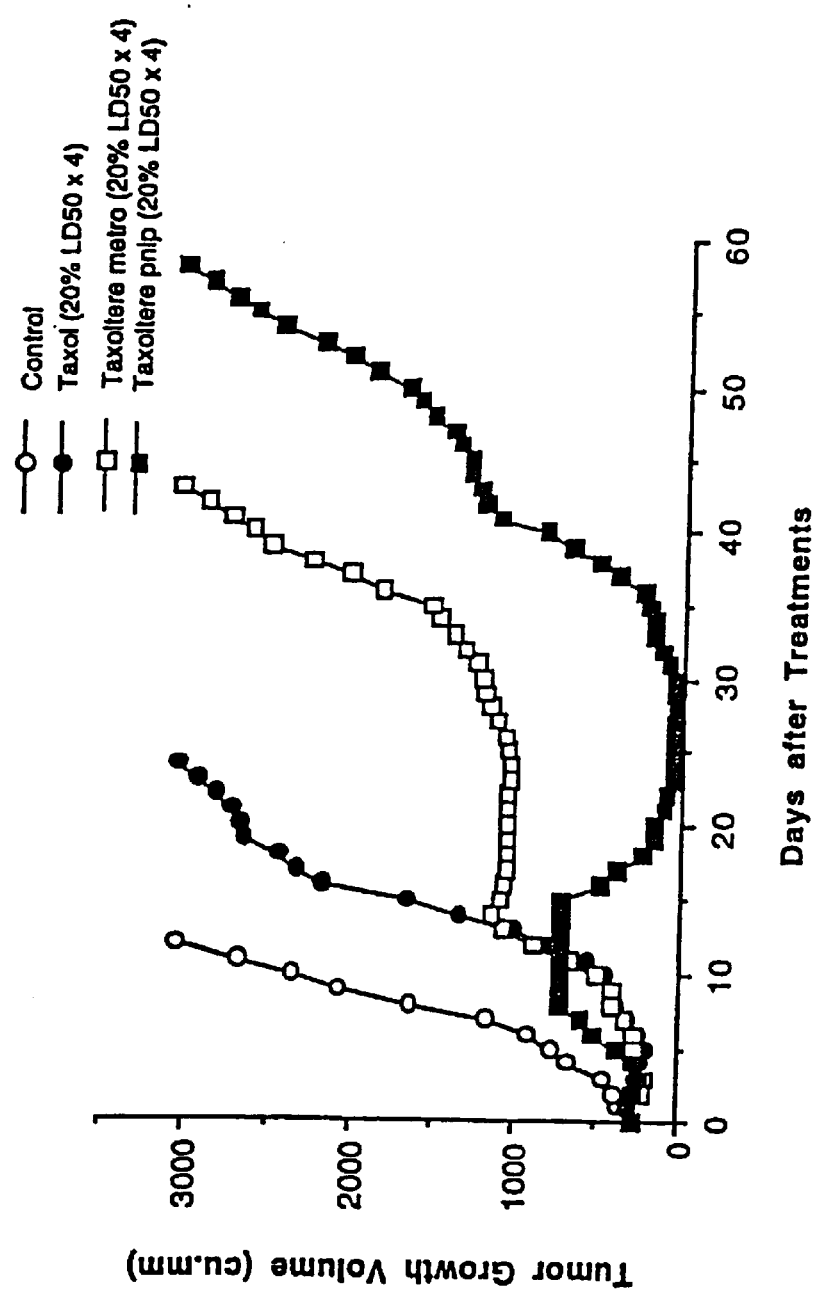
FIG. 7 is a graph depicting the chemotherapeutic effect of low-dose multi-treatment (Q7D×4) with taxol and its analogs on MTG-B mammary tumors for the studies set forth in Example 4.4.
Figure 8:
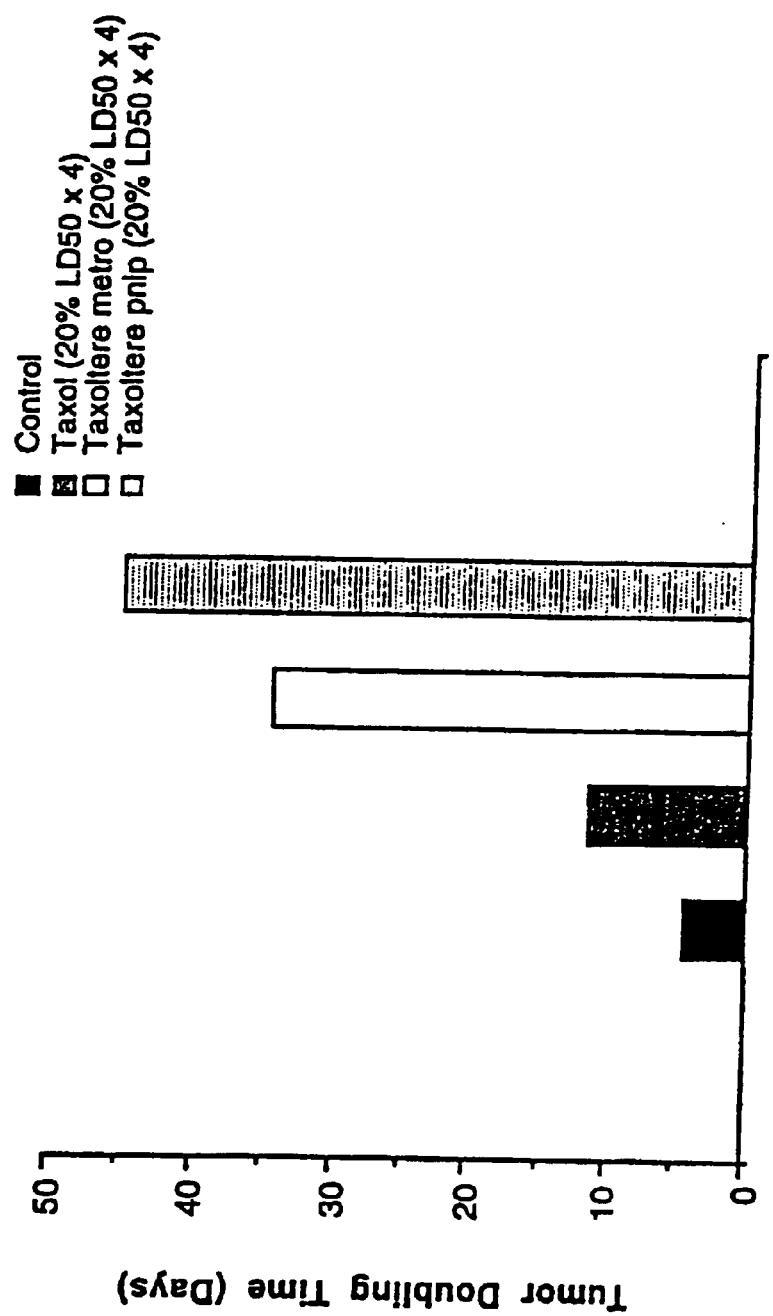
FIG. 8 is a graph depicting the chemotherapeutic effects of low-dose multi-treatment (Q7D×4) with taxol and its analogs on MTG-B mammary tumors for the studies set forth in Example 4.4.
Figure 9:
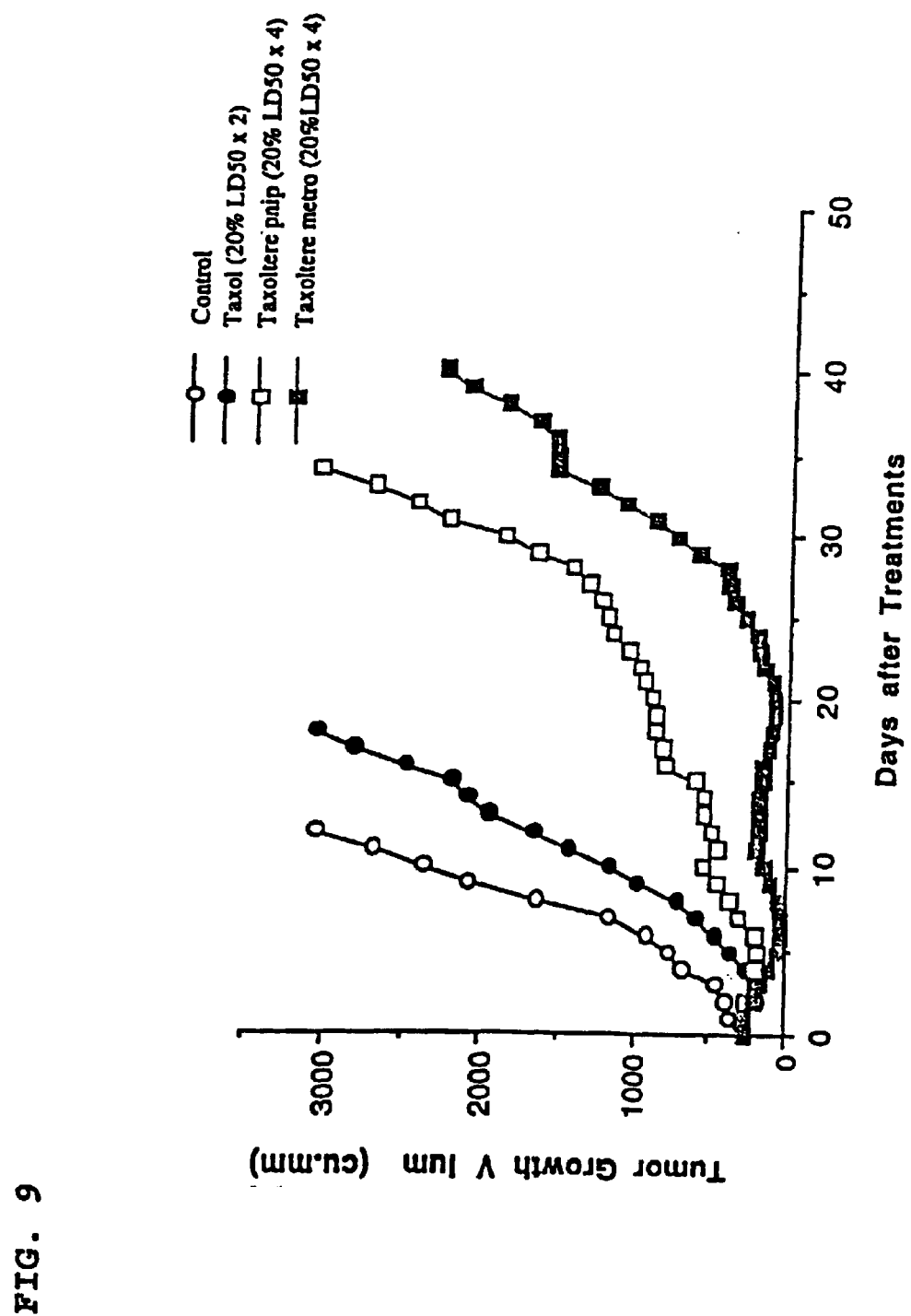
FIGS. 9 and 10 are graphs depicting the chemotherapeutic effects of low-dose multi-treatments (Q11D×4) with taxol and its analogs on MTG-B mammary tumors for the studies set forth in Example 4.4.
Figure 10:
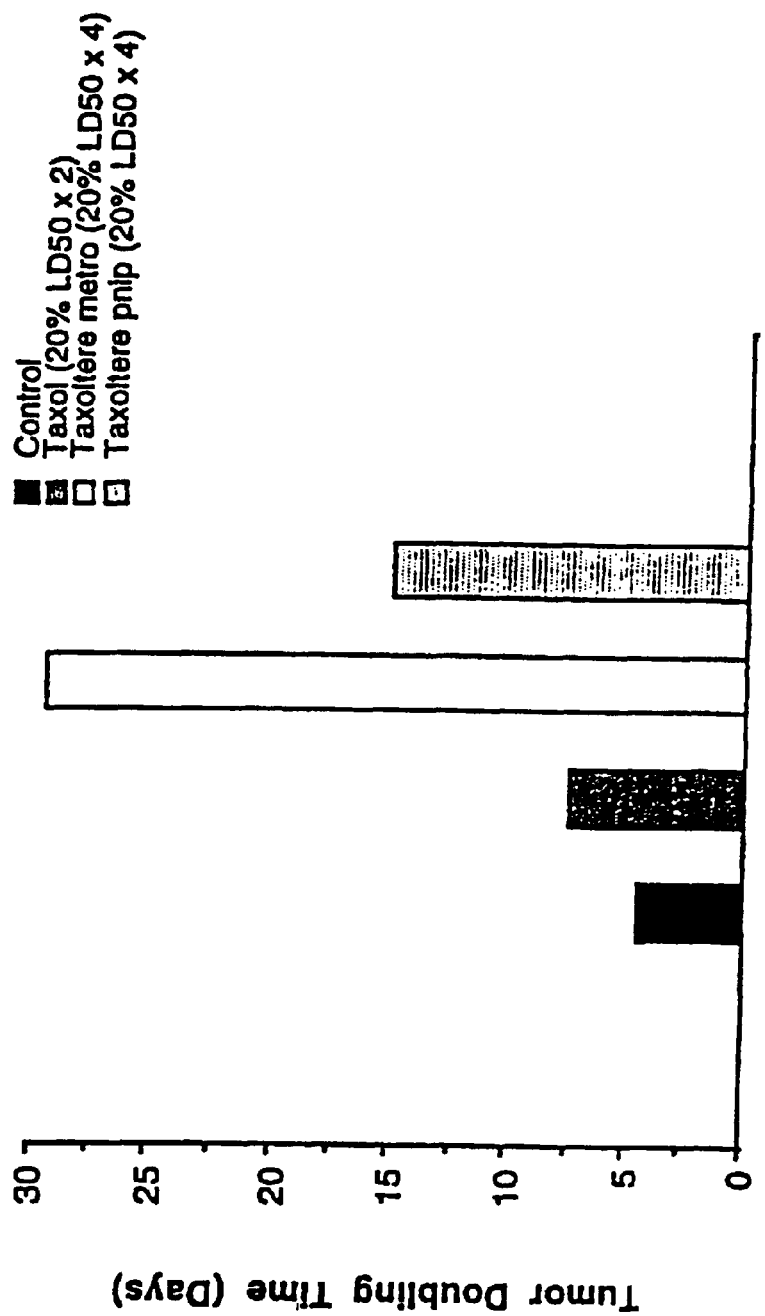

Two experiments in which fractionated lower doses (20% of $LD_{50/5}$) of taxol, taxoltere metro and taxoltere p-nip were administered to MTG-B tumor bearing C3H/Hej mice have been carried out. In the first of these, drugs were administered on a q7dx4 schedule (FIG. 7). As shown in FIG. 8, tumor doubling times are greatly extended by taxoltere metro and are even further extended by taxoltere p-nip on this administration schedule. In the second experiment (FIG. 9), drugs were administered on a q11dx4 schedule. Using this schedule, tumor doubling times (shown in FIG. 10) are again greatly extended, with taxoltere metro producing the better results. Efficacy is positively correlated with frequency of injection (i.e., smaller intervals between injections). On both schedules, taxoltere metro and taxoltere p-nip exhibit significantly stronger antitumor effects than taxol.

Figure 11:
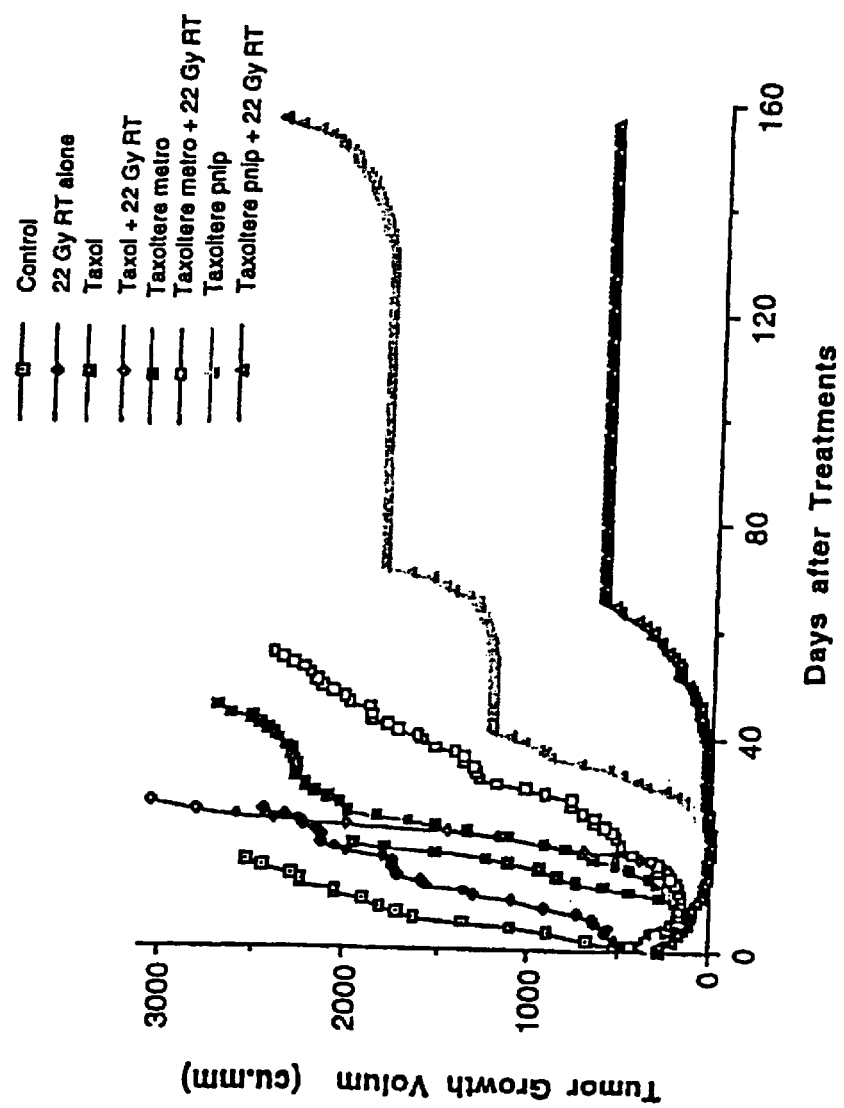
FIG. 11 is a graph depicting in vivo chemotherapeutic radiosensitization of taxoltere metro, taxoltere pnip and taxol on MTG-B mammary tumors (i.p., single dose) for the studies set forth in Example 4.5.
Figure 12:
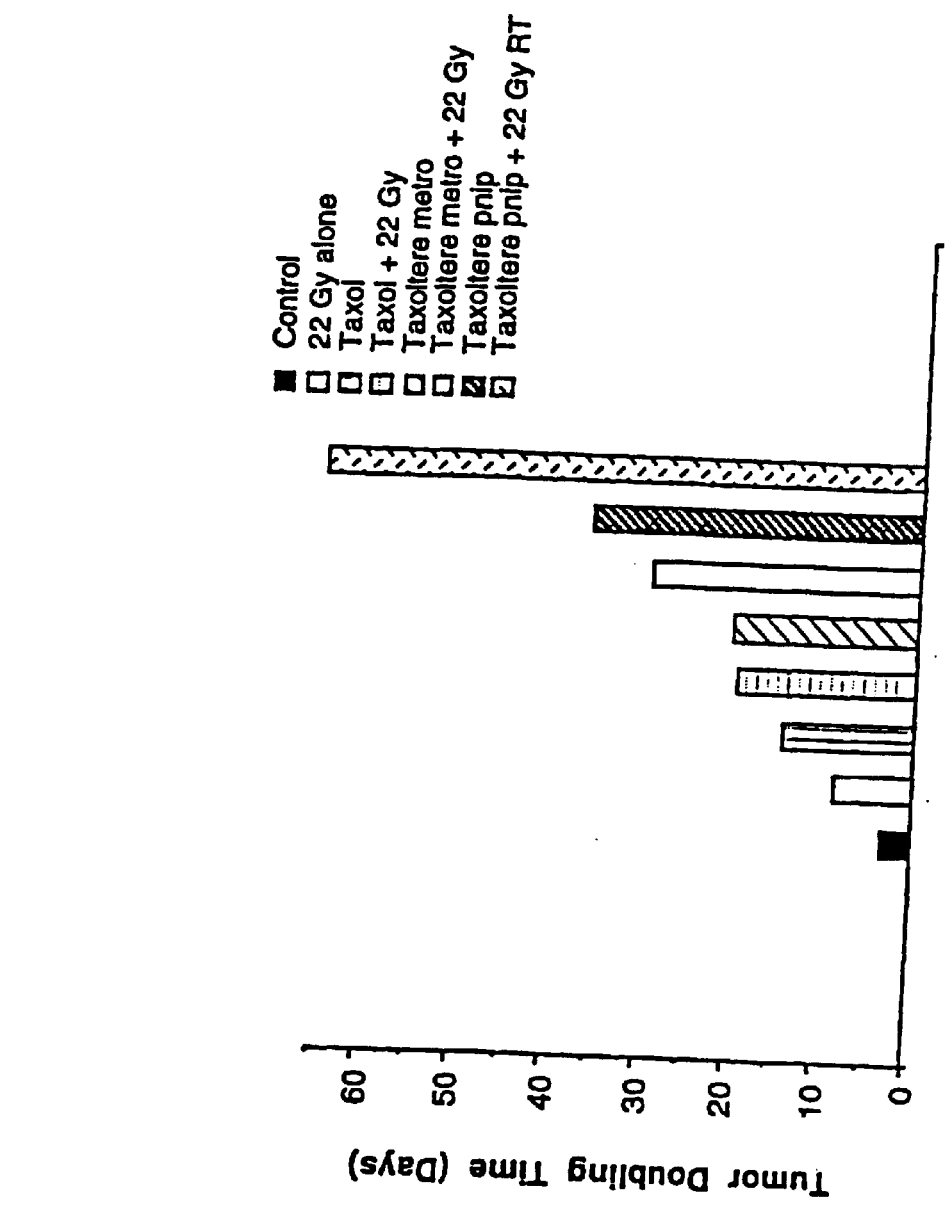
FIG. 12 is a graph depicting the effects of ip taxol, taxoltere metro and taxoltere pnip +/− RT on MTG-B mammary tumors for the studies set forth in Example 4.5.

4.5. In vivo chemotherapeutic radiosensitization. MTG-B tumor bearing C3H/Hej mice received single equitoxic drug doses i.p. (40% of $LD_{50/5}$). One day later the mice were placed in a lead holder (with the tumor-bearing hind leg exposed), and the tumor was subjected to a 22 Gy Xray dose (FIG. 11). As shown in FIG. 12, tumor doubling times (TDT) of 3.5 days (control), 8.5 days (22 Gy Xray exposure alone), 14.5 days (taxol alone), 19.5 days (taxol plus 22 Gy Xray), 20.5 days (taxoltere metro alone), and 29.5 days (taxoltere metro plus 22 Gy Xray) were observed. Equally large effects were observed when mice were given taxoltere metro two hours prior to irradiation (data not shown). Taxoltere p-nip alone (TDT 3D 36.5 days) is even more effective in delaying tumor growth (FIG. 12), and the combination of taxoltere p-nip plus 22 Gy produced a TDT of 65 days.

Figure 13:
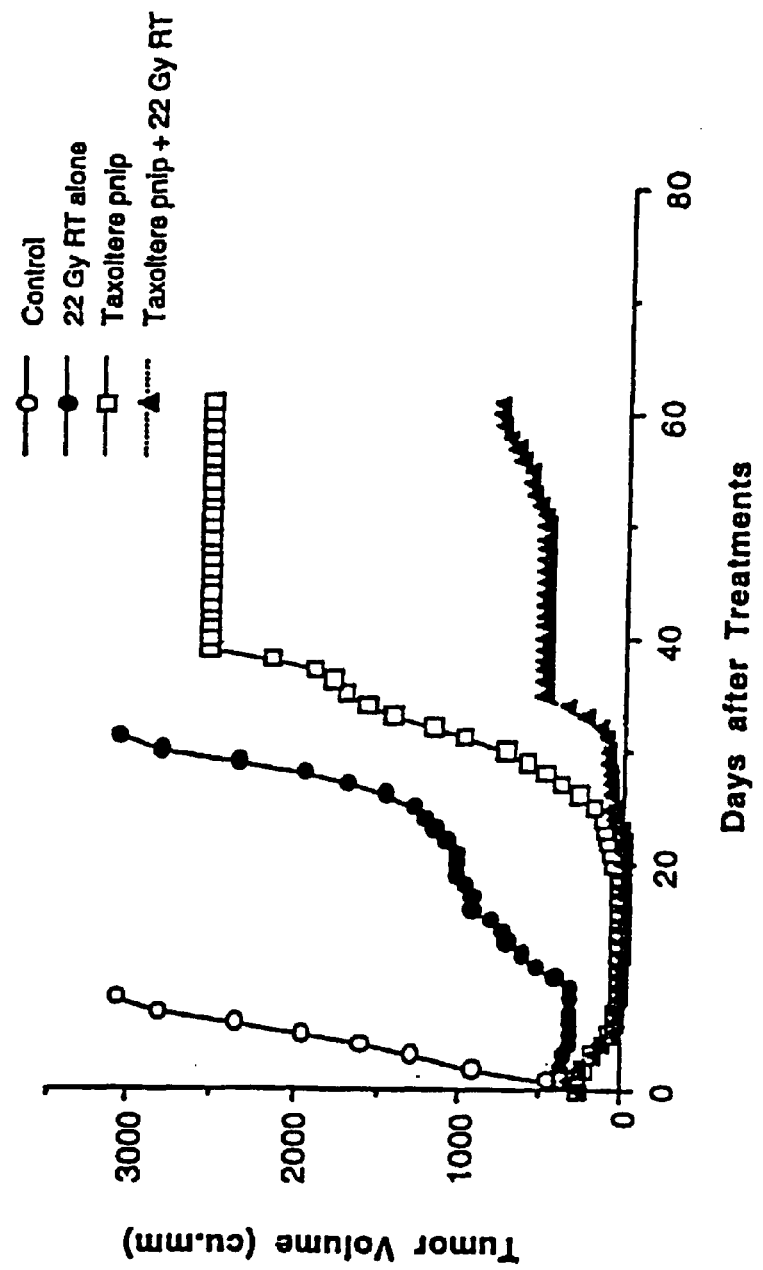
FIGS. 13 and 14 are graphs depicting the effects of taxoltere pnip on MTG-B mammary tumors (i.v., single dose, 24% LD50) for the studies set forth in Example 4.5.
Figure 14:
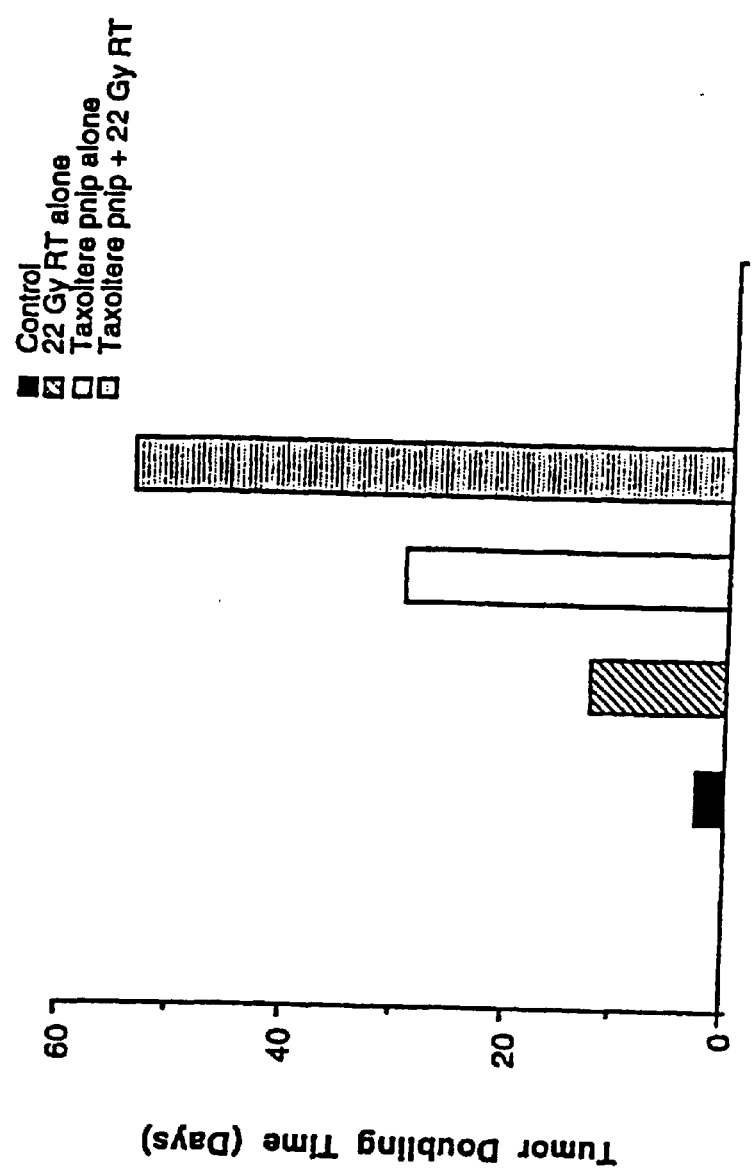

Administration of taxoltere p-nip i.v. (24% of $LD_{50/5}$) (FIG. 13), gave a tumor doubling time of 52 days (FIG. 14), approximately equivalent to the results obtained from i.p. administration.

Figure 15:
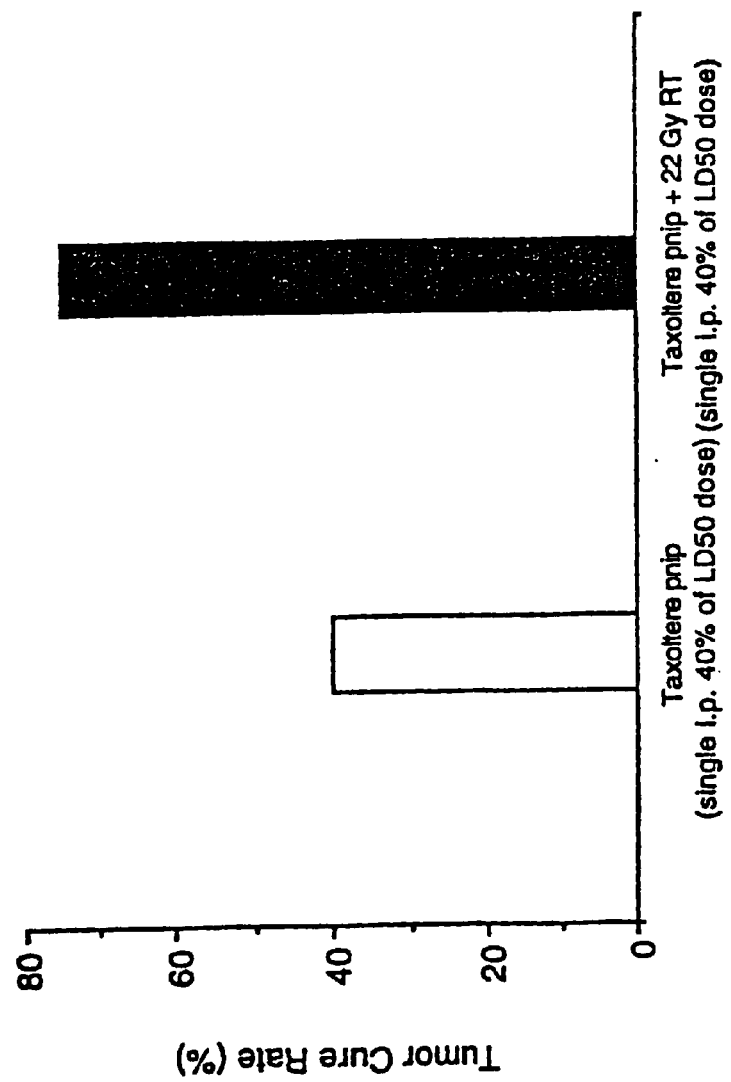
FIG. 15 is a graph depicting the cure rate for taxoltere pnip (i.p., single dose) for the studies set forth in Example 4.6.
Figure 16:
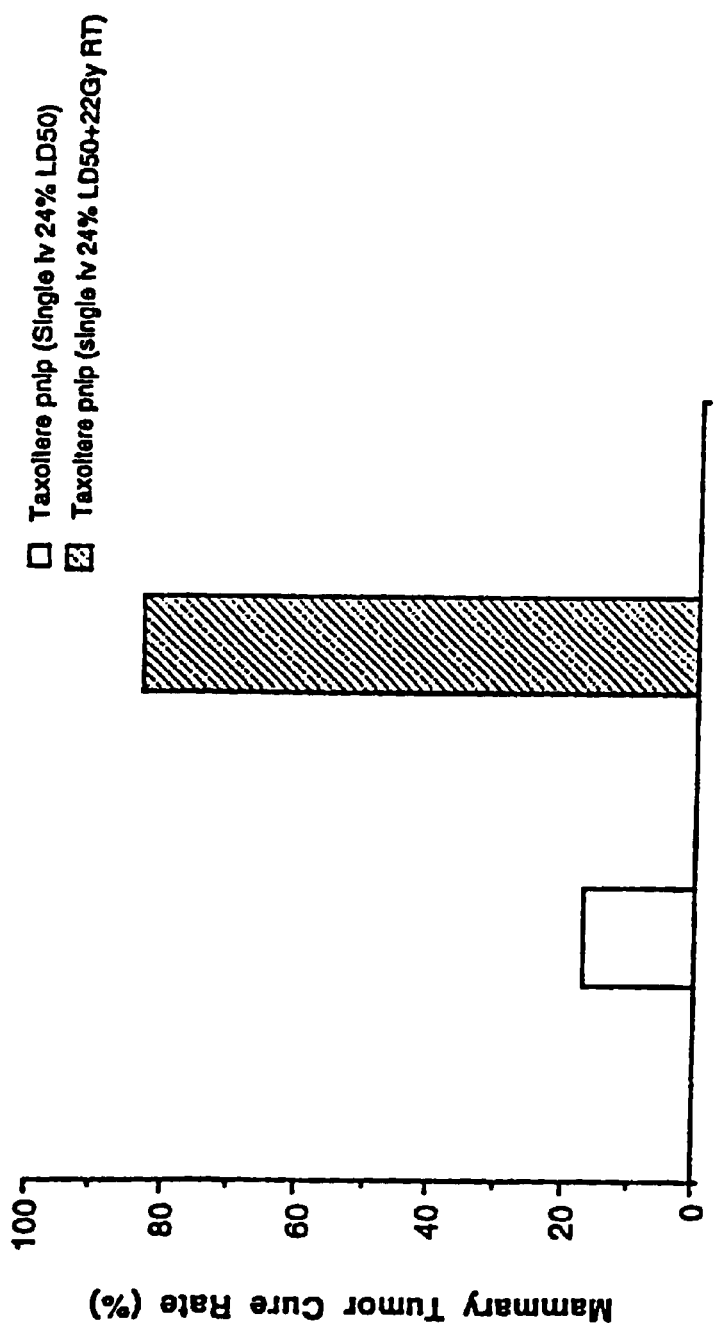
FIGS. 16 and 17 are graphs depicting the cure rate for taxoltere pnip (i.v., single dose) for the studies set forth in Example 4.6.

4.6. Cure Rates. The term "cure" is defined by the U.S. National Cancer Institute as tumor-free survival for at least twice the survival time of control tumor-bearing mice, therefore we have used 28 days tumor-free to define a "cure" in this system. The cure rate is 40% for mice treated i.p. with taxoltere p-nip alone at a single dose, and 75% for the combination of taxoltere p-nip and 22 Gy (FIG. 15). Similarly, a single i.v. injection of taxoltere p-nip alone induces a cure rate of 17%, and an 83% cure rate was observed for the combination of taxoltere p-nip and 22 Gy (FIG. 16), even though this experiment was conducted with a lower dose (24% of $LD_{50/5}$). Although in this latter group one tumor recurred after 40 days, some treated mice have remained tumor-free for more than one year, and still survive.

Figure 17:
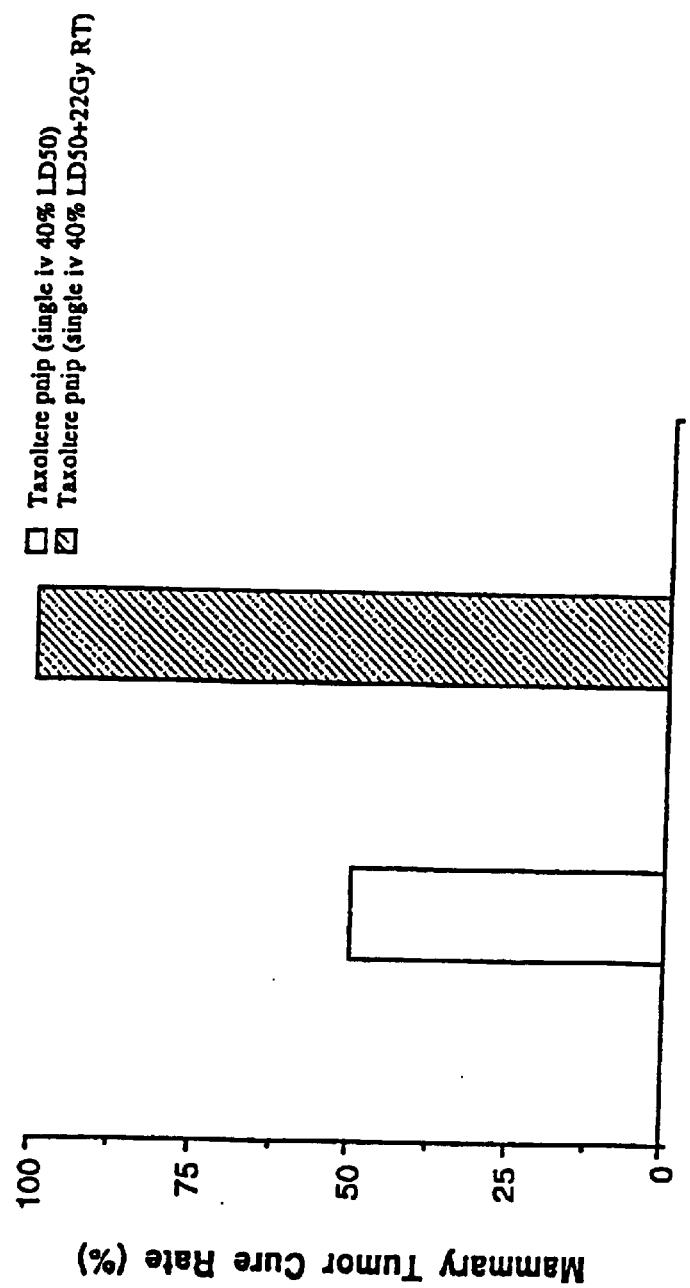
Figure 18:
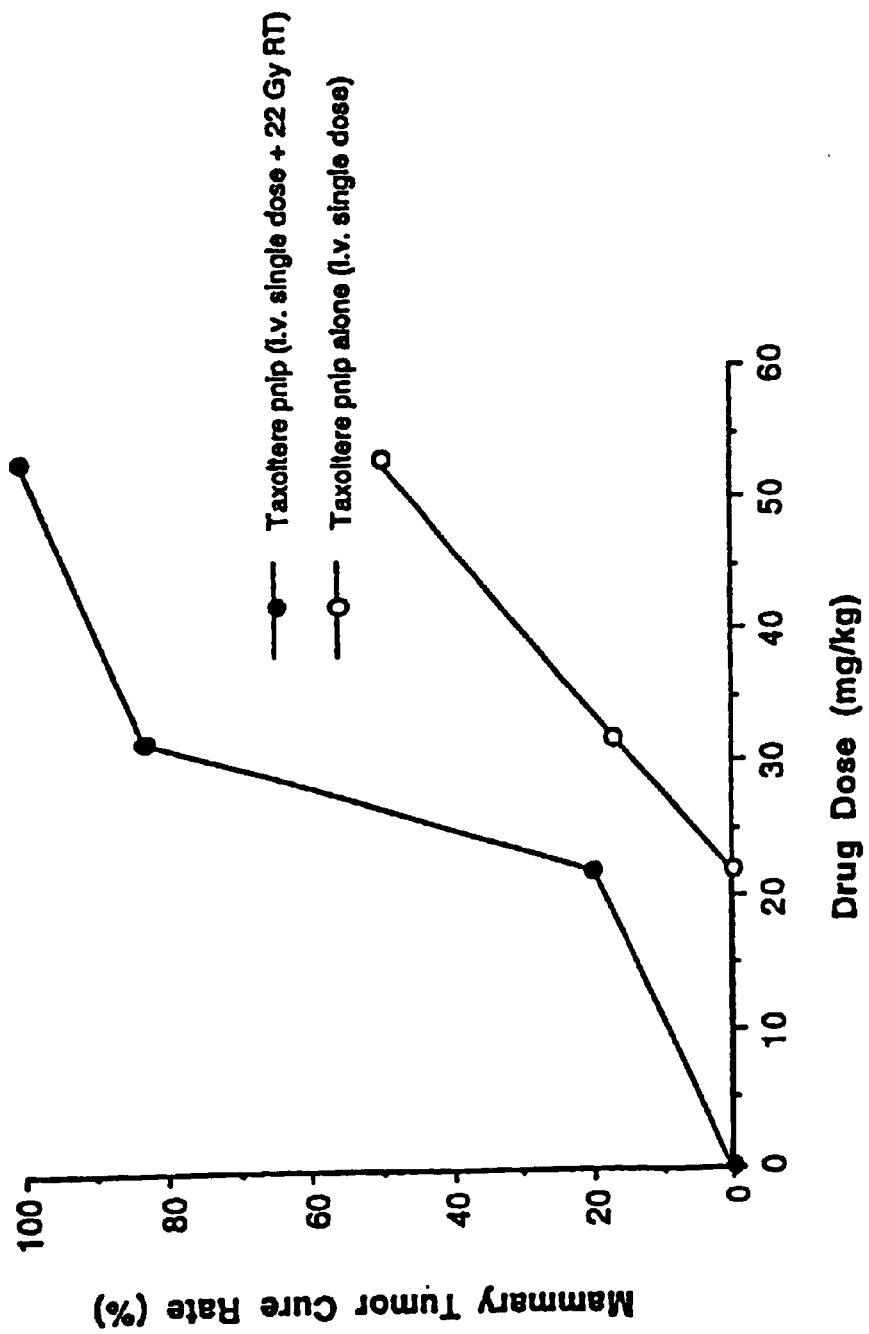
FIG. 18 is a graph depicting the cure rate for taxoltere pnip +/− RT on MTG-B mammary tumors in vivo as a function of drug dose for the studies set forth in Example 4.6.

As shown in FIG. 17, administration of taxoltere p-nip iv at 40% of $LD_{50/5}$ produced a cure rate of 50%, and iv administration of taxoltere p-nip at 40% of $LD_{50/5}$ in combination with 22 Gy radiation produced a cure rate of 100%. Cure rate as a function of drug dose is shown in FIG. 18.

In view of the above, it will be seen that the several objects of the invention are achieved and other advantageous results attained.

As various changes could be made in the above compounds and methods without departing from the scope of the invention it is intended that all matter contained in the above description shall be interpreted as illustrative and not in a limiting sense.

What is claimed is:

1. A compound comprising a taxane containing at least 2 electron-affinic radiosensitizing functional groups.

2. The compound of claim 1 wherein at least one of the radiosensitizing groups is a nitro-substituted carbocyclic or heterocyclic aromatic moiety which is attached to the C2, C4, C7, C9, C10 or C14 position of the taxane.

3. The compound of claim 1 wherein said radiosensitizing groups are independently selected from nitro-substituted carbocyclic and heterocyclic aromatic moieties and and wherein at least one of said radiosensitizing groups is attached to the C2, C4, C7, C9, C10 or C14 position of the taxane.

4. A compound corresponding to the structure:

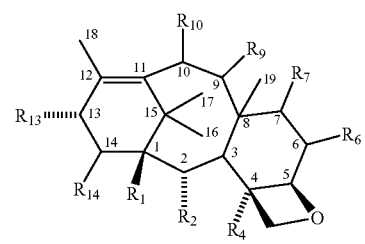

wherein

M comprises ammonium or is a metal;

$R_1$ is hydrogen or hydroxy;

$R_2$ is $-OT_2$, $-OCOZ_2$, $-OCOOZ_2$, $RSG_1$ or $RSG_2$;

$R_4$ is $-OT_4$, $-OCOZ_4$, $-OCOOZ_4$, $RSG_1$ or $RSG_2$;

$R_7$ is hydrogen, halogen, $-OT_7$, $-OCOZ_7$, $-OCOOZ_7$, $RSG_1$ or $RSG_2$;

$R_9$ is hydrogen, keto, $-OT_9$, $-OCOZ_9$, $-OCOOZ_9$, $RSG_1$ or $RSG_2$;

$R_{10}$ is hydrogen, keto, $-OT_{10}$, $-OCOZ_{10}$, $-OCOOZ_{10}$, $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

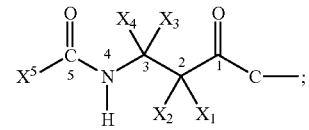

$R_{14}$ is hydrogen, hydroxy, protected hydroxy, $RSG_1$ or $RSG_2$;

$T_2$, $T_4$, $T_7$, $T_9$ and $T_{10}$ are independently hydrogen or hydroxy protecting group;

$X_1$ is $-OX_6$;

$X_2$ is hydrogen, hydrocarbon, heterosubstituted hydrocarbon, heteroaryl, or heterosubstituted heteroaryl;

$X_3$ is alkyl, heterosubstituted alkyl, alkenyl, heterosubstituted alkenyl, alkynyl, heterosubstituted alkynyl, phenyl, heteroaryl, or heterosubstituted heteroaryl;

$X_4$ is hydrogen, alkyl, heterosubstituted alkyl, alkenyl, heterosubstituted alkenyl, alkynyl, heterosubstituted alkynyl, phenyl, heteroaryl, or heterosubstituted heteroaryl;

$X_5$ is $-X_{10}$, $-OX_{10}$, $-SX_{11}$, or $-NX_8X_{11}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is alkyl, heterosubstituted alkyl, alkenyl, heterosubstituted alkenyl, alkynyl, heterosubstituted alkynyl, phenyl, heteroaryl, or heterosubstituted heteroaryl;

$X_{11}$ is hydrocarbon, heterosubstituted hydrocarbon, heteroaryl, heterosubstituted heteroaryl, $RSG_1$ or $RSG_2$;

$Z_2$, $Z_4$, $Z_7$, $Z_9$ and $Z_{10}$ are independently hydrocarbon, heterosubstituted hydrocarbon, heteroaryl, or heterosubstituted heteroaryl;

$RSG_1$ is an electron-affinic moiety;

$RSG_2$ is —L—$(RSG_1)_n$;

L is a linker comprising a chain of 1 to 30 atoms in the chain, the atoms being selected from the group consisting of C, O, N, S, Si, and P; and n is an integer greater than or equal to 1;

provided that the compound contains at least one radiosensitizing group attached to the C2, C4, C7, C9, C10, C14, C3' or C5' position of the compound.

5. The compound of claim 4 wherein $RSG_1$ is an electron-affinic group selected from the group consisting of (i) carbocyclic and heterocyclic aromatic moieties which possess one or more carbonyl, trifluoromethyl, halogen, nitro, sulfonyl, sulfinyl, phosphoryl, oxide or cyano groups, (ii) heterocyclic aromatic moieties containing two or more heteroatoms, (iii) metal complexes, and (iv) organo-metallic groups in which the metal is covalently bonded to carbon.

6. The compound of claim 4 wherein $RSG_1$ is selected from the group consisting of imidazoles, triazoles, pyridines, benzamides, nicotinamides, benzotriazine oxides, furans, thiophenes, oxazoles and thiozoles possessing one or more carbonyl, trifluoromethyl, halogen, nitro, sulfonyl, sulfinyl, phosphoryl, oxide or cyano groups.

7. The compound of claim 4 wherein $R_1$ is hydrogen or hydroxy;

$R_2$ is —$OCOZ_2$, $RSG_1$, or $RSG_2$;

$R_4$ is —$OCOZ_4$, $RSG_1$ or $RSG_2$;

$R_7$ is hydrogen, halogen, —$OT_7$, —$OCOZ_7$, $RSG_1$ or $RSG_2$;

$R_9$ is hydrogen, keto, —$OT_9$, —$OCOZ_9$, $RSG_1$ or $RSG_2$;

$R_{10}$ is hydrogen, keto, —$OT_{10}$, —$OCOZ_{10}$, $RSG_1$ or $RSG_2$;

$R_{13}$ is

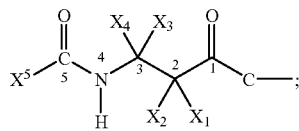

$R_{14}$ is hydrogen, hydroxy or protected hydroxy;

$T_2$, $T_4$, $T_7$, $T_9$ and $T_{10}$ are independently hydrogen or hydroxy protecting group;

$X_1$ is —$OX_6$;

$X_2$ is hydrogen;

$X_3$ is alkyl, alkenyl, phenyl, heteroaryl, or heterosubstituted heteroaryl;

$X_4$ is hydrogen, hydrocarbon, heteroaryl or heterosubstituted heteroaryl;

$X_5$ is —$X_{10}$, —$OX_{10}$, —$SX_{11}$, or —$NX_8X_{11}$;

$X_6$ is hydrogen or hydroxy protecting group;

$X_8$ is hydrogen, hydrocarbon, heterosubstituted hydrocarbon, $RSG_1$ or $RSG_2$;

$X_{10}$ is alkyl, alkenyl, phenyl, heteroaryl, or heterosubstituted heteroaryl;

$Z_2$, $Z_4$, $Z_7$, $Z_9$ and $Z_{10}$ are independently hydrocarbon, heterosubstituted hydrocarbon, heteroaryl, or heterosubstituted heteroaryl;

$RSG_1$ is an electron-affinic moiety;

$RSG_2$ is —L—$(RSG_1)_n$;

L is a linker comprising a chain of 1 to 10 atoms in the chain, the atoms being selected from the group consisting of C, O, N, S, Si, and P; and n is 1 or 2.

8. The compound of claim 4 wherein $RSG_1$ is a heterocyclic aromatic moiety containing two or more heteroatoms.

9. The compound of claim 4 wherein $RSG_1$ is a metal complex.

10. The compound of claim 4 wherein $RSG_1$ is selected from the group consisting imidazoles, triazoles, pyridines, benzamides, furans, thiophenes, oxazoles and thiozoles possessing one or more nitro groups.

11. A compound corresponding to the structure:

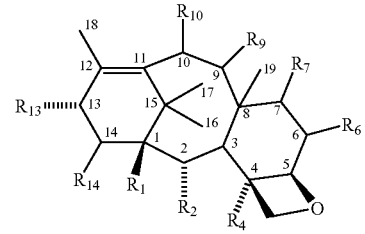

wherein

M comprises ammonium or is a metal;

$R_1$ is hydrogen or hydroxy;

$R_2$ is $RSG_1$ or $RSG_2$;

$R_4$ is —$OT_4$, —$OCOZ_4$, $RSG_1$ or $RSG_2$;

$R_7$ is hydrogen, halogen, —$OT_7$, —$OCOZ_7$, —$OCOOZ_7$ $RSG_1$ or $RSG_2$;

$R_9$ is hydrogen, keto, —$OT_9$, —$OCOZ_9$, —$OCOOZ_9$, $RSG_1$ or $RSG_2$;

$R_{10}$, is hydrogen, keto, —$OT_{10}$, —$OCOZ_{10}$, —$OCOOZ_{10}$, $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

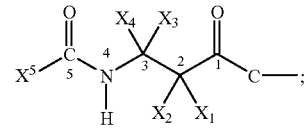

$R_{14}$ is hydrogen, hydroxy, protected hydroxy, $RSG_1$ or $RSG_2$;

$T_2$, $T_4$, $T_7$, $T_9$ and $T_{10}$ are independently hydrogen or hydroxy protecting group;

$X_1$ is —$OX_6$;

$X_2$ is hydrogen, hydrocarbon, heterosubstituted hydrocarbon, heteroaryl, or heterosubstituted heteroaryl;

$X_3$ and $X_4$ are independently hydrogen, hydrocarbon, heterosubstituted hydrocarbon, heteroaryl, heterosubstituted heteroaryl or $RSG_1$;

$X_5$ is $-X_{10}$, $-OX_{10}$, $-SX_{10}$, or $-NX_8X_{10}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_4$, $Z_7$, $Z_9$ and $Z_{10}$ are independently hydrocarbon, heterosubstituted hydrocarbon, heteroaryl, or heterosubstituted heteroaryl;

$RSG_1$ is an electron-affinic moiety;

$RSG_2$ is $-L-(RSG_1)_n$;

L is a linker comprising a chain of 1 to 30 atoms in the chain, the atoms being selected from the group consisting of C, O, N, S, Si, and P; and n is an integer greater than or equal to 1.

12. A compound corresponding to the structure:

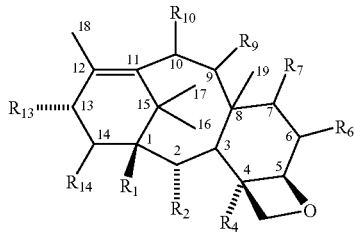

wherein

M comprises ammonium or is a metal;

$R_1$ is hydrogen or hydroxy;

$R_2$ is $-OT_2$, $-OCOZ_2$, $-OCOOZ_2$, $RSG_1$ or $RSG_2$;

$R_4$ is $RSG_1$ or $RSG_2$;

$R_7$ is hydrogen, halogen, $-OT_7$, $-OCOZ_7$, $-OCOOZ_7$, $RSG_1$ or $RSG_2$;

$R_9$ is hydrogen, keto, $-OT_9$, $-OCOZ_9$, $-OCOOZ_9$, $RSG_1$ or $RSG_2$;

$R_{10}$ is hydrogen, keto, $-OT_{10}$, $-OCOZ_{10}$, $-OCOOZ_{10}$, $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

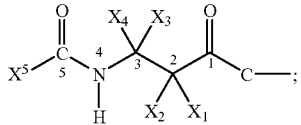

$R_{14}$ is hydrogen, hydroxy, protected hydroxy, $RSG_1$ or $RSG_2$;

$T_2$, $T_4$, $T_7$, $T_9$ and $T_{10}$ are independently hydrogen or hydroxy protecting group;

$X_1$ is $-OX_6$;

$X_2$ is hydrogen, hydrocarbon, heterosubstituted hydrocarbon, heteroaryl, or heterosubstituted heteroaryl;

$X_3$ and $X_4$ are independently hydrogen, hydrocarbon, heterosubstituted hydrocarbon, heteroaryl, heterosubstituted heteroaryl, or $RSG_1$;

$X_9$ is $-X_{10}$, $-OX_{10}$, $-SX_{10}$, or $-NX_8X_{10}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_2$, $Z_7$, $Z_9$ and $Z_{10}$ are independently hydrocarbon, heterosubstituted hydrocarbon, heteroaryl, or heterosubstituted heteroaryl;

$RSG_1$ is an electron-affinic moiety;

$RSG_2$ is $-L-(RSG_1)_n$;

L is a linker comprising a chain of 1 to 30 atoms in the chain, the atoms being selected from the group consisting of C, O, N, S, Si, and P; and n is an integer greater than or equal to 1.

13. A compound corresponding to the structure:

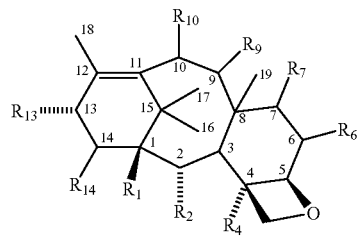

wherein

M comprises ammonium or is a metal;

$R_1$ is hydrogen or hydroxy;

$R_2$ is $-OT_2$, $-OCOZ_2$, $-OCOOZ_2$, $RSG_1$ or $RSG_2$;

$R_4$ is $-OT_4$, $-OCOZ_4$, $-OCOOZ_4$, $RSG_1$ or $RSG_2$;

$R_7$ is $RSG_1$ or $RSG_2$;

$R_9$ is hydrogen, keto, $-OT_9$, $-OCOZ_9$, $-OCOOZ_9$, $RSG_1$ or $RSG_2$;

$R_{10}$ is hydrogen, keto, $-OT_{10}$, $-OCOZ_{10}$, $-OCOOZ_{10}$, $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

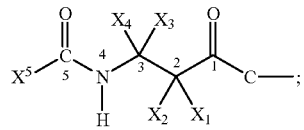

$R_{14}$ is hydrogen, hydroxy, protected hydroxy, $RSG_1$ or $RSG_2$;

$T_2$, $T_4$, $T_9$ and $T_{10}$ are independently hydrogen or hydroxy protecting group;

$X_1$ is $-OX_6$;

$X_2$ is hydrogen, hydrocarbon, heterosubstituted hydrocarbon, heteroaryl, or heterosubstituted heteroaryl;

$X_3$ and $X_4$ are independently hydrogen, hydrocarbon, heterosubstituted hydrocarbon, heteroaryl, heterosubstituted heteroaryl or $RSG_1$;

$X_5$ is $-X_{10}$, $-OX_{10}$, $-SX_{10}$, or $-NX_8X_{10}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_2$, $Z_4$, $Z_9$ and $Z_{10}$ are independently hydrocarbon, heterosubstituted hydrocarbon, heteroaryl, or heterosubstituted heteroaryl;

$RSG_1$ is an electron-affinic moiety;

$RSG_2$ is $-L-(RSG_1)_n$;

L is a linker comprising a chain of 1 to 30 atoms in the chain, the atoms being selected from the group consisting of C, O, N, S, Si, and P; and n is an integer greater than or equal to 1.

14. A compound corresponding to the structure:

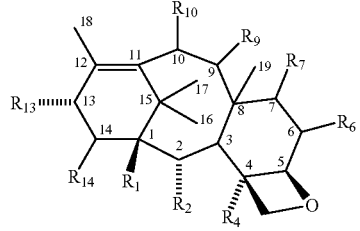

wherein

M comprises ammonium or is a metal;

$R_1$ is hydrogen or hydroxy;

$R_2$ is $-OT_2$, $-OCOZ_2$, $-OCOOZ_2$, $RSG_1$ or $RSG_2$;

$R_4$ is $-OT_4$, $-OCOZ_4$, $-OCOOZ_4$, $RSG_1$ or $RSG_2$;

$R_7$ is hydrogen, keto, $-OT_7$, $-OCOZ_7$, $-OCOOZ_7$, $RSG_1$ or $RSG_2$;

$R_9$ is $RSG_1$ or $RSG_2$;

$R_{10}$ is hydrogen, keto, $-OT_{10}$, $-OCOZ_{10}$, $-OCOZ_{10}$, $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

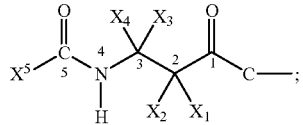

$R_{14}$ is hydrogen, hydroxy, protected hydroxy, $RSG_1$ or $RSG_2$;

$T_2$, $T_4$, $T_7$ and $T_{10}$ are independently hydrogen or hydroxy protecting group;

$X_1$ is $-OX_6$;

$X_2$ is hydrogen, hydrocarbon, heterosubstituted hydrocarbon, heteroaryl, or heterosubstituted heteroaryl;

$X_3$ and $X_4$ are independently hydrogen, hydrocarbon, heterosubstituted hydrocarbon, heteroaryl, heterosubstituted heteroaryl or $RSG_1$;

$X_5$ is $-X_{10}$, $-OX_{10}$, $-SX_{10}$, or $-NX_8X_{10}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_2$, $Z_4$, $Z_7$ and $Z_{10}$ are independently hydrocarbon, heterosubstituted hydrocarbon, heteroaryl, or heterosubstituted heteroaryl;

$RSG_1$ is an electron-affinic moiety;

$RSG_2$ is $-L-(RSG_1)_n$;

L is a linker comprising a chain of 1 to 30 atoms in the chain, the atoms being selected from the group consisting of C, O, N, S, Si, and P; and n is an integer greater than or equal to 1.

15. A compound corresponding to the structure:

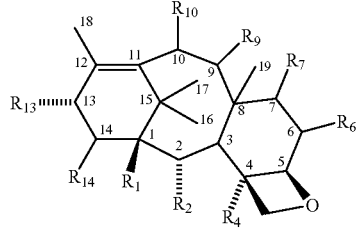

wherein

M comprises ammonium or is a metal;

$R_1$ is hydrogen or hydroxy;

$R_2$ is $-OT_2$, $-OCOZ_2$, $-OCOOZ_2$, $RSG_1$ or $RSG_2$;

$R_4$ is $-OT_4$, $-OCOZ_4$, $-OCOOZ_9$ $RSG_1$ or $RSG_2$;

$R_7$ is hydrogen, keto, $-OT_7$, $-OCOZ_7$, $-OCOOZ_7$, $RSG_1$ or $RSG_2$;

$R_9$ is hydrogen, keto, $-OT_9$, $-OCOZ_9$, $-OCOOZ_9$, $RSG_1$ or $RSG_2$;

$R_{10}$ is $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

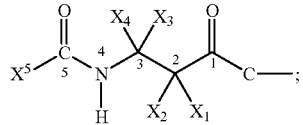

$R_{14}$ is hydrogen, hydroxy, protected hydroxy, $RSG_1$ or $RSG_2$;

$T_2$, $T_4$, $T_7$ and $T_9$ are independently hydrogen or hydroxy protecting group;

$X_1$ is $-OX_6$;

$X_2$ is hydrogen, hydrocarbon, heterosubstituted hydrocarbon, heteroaryl, or heterosubstituted heteroaryl;

$X_3$ and $X_4$ are independently hydrogen, hydrocarbon, heterosubstituted hydrocarbon, heteroaryl, heterosubstituted heteroaryl or $RSG_1$;

$X_5$ is $-X_{10}$, $-OX_{10}$, $-SX_{10}$, or $-NX_8X_{10}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_2$, $Z_4$, $Z_7$ and $Z_9$ are independently hydrocarbon, heterosubstituted hydrocarbon, heteroaryl, or heterosubstituted heteroaryl;

$RSG_1$ is an electron-affinic moiety;

$RSG_2$ is $-L-(RSG_1)_n$;

L is a linker comprising a chain of 1 to 30 atoms in the chain, the atoms being selected from the group consisting of C, O, N, S, Si, and P; and n is an integer greater than or equal to 1.

16. A compound corresponding to the structure:

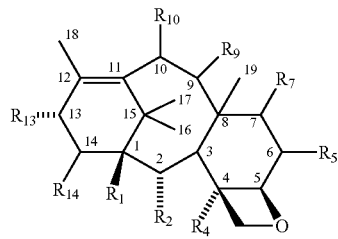

wherein

M comprises ammonium or is a metal;

$R_1$ is hydrogen or hydroxy;

$R_2$ is $-OT_2$, $-OCOZ_2$, $-OCOOZ_2$, $RSG_1$ or $RSG_2$;

$R_4$ is $-OT_4$, $-OCOZ_4$, $-OCOOZ_4$, $RSG_1$ or $RSG_2$;

$R_7$ is hydrogen, keto, $-OT_7$, $-OCOZ_7$—$OCOOZ_7$, $RSG_1$ or $RSG_2$;

$R_9$ is hydrogen, keto, $-OT_9$, $-OCOZ_9$, $-OCOOZ_9$, $RSG_1$ or $RSG_2$;

$R_{10}$ is hydrogen, keto, $-OT_{10}$, $-OCOZ_{10}$, $-OCOOZ_{10}$, $RSG_1$ or $RSG_2$;

$R_7$, $R_9$, and $R_{10}$ independently have the alpha or beta stereochemical configuration;

$R_{13}$ is hydroxy, protected hydroxy, keto, MO- or

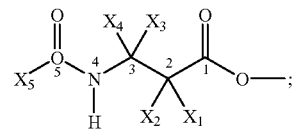

$R_{14}$ is $RSG_1$ or $RSG_2$;

$T_2$, $T_4$, $T_7$, $T_9$ and $T_{10}$ are independently hydrogen or hydroxy protecting group;

$X_1$ is $-OX_6$;

$X_2$ is hydrogen, hydrocarbon, heterosubstituted hydrocarbon, heteroaryl, or heterosubstituted heteroaryl;

$X_3$ and $X_4$ are independently hydrogen, hydrocarbon, heterosubstituted hydrocarbon, heteroaryl, heterosubstituted heteroaryl or $RSG_1$;

$X_5$ is $-X_{10}$, $-OX_{10}$, $-SX_{10}$, or $-NX_8X_{10}$;

$X_6$ is hydrogen, hydrocarbon, heterosubstituted hydrocarbon, heteroaryl, heterosubstituted heteroaryl, hydroxy protecting group or a functional group which increases the water solubility of the taxane derivative;

$X_8$ is hydrogen, hydrocarbon, heterosubstituted hydrocarbon, $RSG_1$ or $RSG_2$;

$X_{10}$ is hydrocarbon, heterosubstituted hydrocarbon, heteroaryl, heterosubstituted heteroaryl, $RSG_1$ or $RSG_2$;

$Z_2$, $Z_4$, $Z_7$, $Z_9$ and $Z_{10}$ are independently hydrocarbon, heterosubstituted hydrocarbon, heteroaryl or heterosubstituted heteroaryl;

$RSG_1$ is an electron-affinic moiety;

$RSG_2$ is $-L-(RSG_1)_n$;

L is a linker comprising a chain of 1 to 30 atoms in the chain, the atoms being selected from the group consisting of C, O, N, S, Si, and P; and n is an integer greater than or equal to 1.

17. A method of killing tumor cells in a warm-blooded animal, the method comprising:

(a) administering to the warm-blooded animal a taxane containing an electron-affinic radiosensitizing functional group, (b) followed by, after a time interval sufficient to enhance radiosensitization of the tumor cells, irradiating the tumor cells with a dose of radiation effective to kill the tumor cells.

* * * * *